United States Patent
Gross et al.

(10) Patent No.: US 8,821,592 B1
(45) Date of Patent: Sep. 2, 2014

(54) OXIDATION DYE PRECURSORS

(75) Inventors: Wibke Gross, Hueckelhoven (DE); Ralph Nemitz, Juechen (DE); Astrid Kroos, Monheim (DE)

(73) Assignee: Henkel AG & Co. KGaA, Dusseldorf (DE)

( * ) Notice: Subject to any disclaimer, the term of this patent is extended or adjusted under 35 U.S.C. 154(b) by 0 days.

(21) Appl. No.: 14/234,105

(22) PCT Filed: May 29, 2012

(86) PCT No.: PCT/EP2012/060035
§ 371 (c)(1),
(2), (4) Date: Mar. 4, 2014

(87) PCT Pub. No.: WO2013/013861
PCT Pub. Date: Jan. 31, 2013

(30) Foreign Application Priority Data

Jul. 22, 2011 (DE) .......................... 10 2011 079 643

(51) Int. Cl.
| | | |
|---|---|---|
| *A61Q 5/10* | (2006.01) | |
| *C07C 211/63* | (2006.01) | |
| *A61K 8/49* | (2006.01) | |
| *C07C 211/53* | (2006.01) | |
| *C07D 295/13* | (2006.01) | |
| *A61K 8/41* | (2006.01) | |

(52) U.S. Cl.
CPC ............... *A61K 8/4946* (2013.01); *A61Q 5/10* (2013.01); *C07C 211/63* (2013.01); *A61K 8/494* (2013.01); *C07C 211/53* (2013.01); *C07D 295/13* (2013.01); *A61K 8/416* (2013.01)

USPC ................ 8/405; 8/406; 8/408; 8/410; 8/411; 8/412; 8/565; 8/573; 8/570; 8/696

(58) Field of Classification Search
CPC ......... A61Q 5/10; A61K 8/416; A61K 8/494; A61K 8/4946
USPC ............. 8/405, 406, 408, 411, 412, 565, 570, 8/573, 606
See application file for complete search history.

(56) References Cited

U.S. PATENT DOCUMENTS 7,303,591 B2 * 12/2007 Greaves et al. ................... 8/405

FOREIGN PATENT DOCUMENTS

| EP | 1396486 A1 | 3/2004 |
| EP | 1739079 A1 | 1/2007 |
| EP | 1739084 A1 | 1/2007 |
| FR | 2864964 A1 | 7/2005 |

OTHER PUBLICATIONS

STIC Search Report dated Jun. 5, 2014.*
International Search Report and Written Opinion issued in PCT/EP2012060035 dated Feb. 13, 2014.

* cited by examiner

*Primary Examiner* — Eisa Elhilo
(74) *Attorney, Agent, or Firm* — Ingrassia Fisher & Lorenz, P.C.

(57) ABSTRACT

An agent for the oxidative dyeing of keratinous fibers is provided. The agent contains, as a developer-type oxidation dye precursor, a compound of Formula (I) that carries at least one cationic charge in Y.

14 Claims, No Drawings

OXIDATION DYE PRECURSORS

CROSS-REFERENCE TO RELATED APPLICATION

The present disclosure is a U.S. National Stage entry under 35 U.S.C. §371 based on International Application No. PCT/EP2012/060035, filed May 29, 2012 which was published under PCT Article 21(2) and which claims priority to German Patent Application No. DE 10 2011 079 643.6 filed on Jul. 22, 2011, which is incorporated herein in its entirety by reference.

TECHNICAL FIELD

The technical field relates to an agent for the oxidative color modification of keratin-containing fibers, especially human hair, said agent comprising certain cationic, dimeric p-phenylenediamine derivatives, the use of these agents as color modifying agents for keratin-containing fibers in order to improve the coloration results as well as a method for dyeing keratin-containing fibers, especially human hair.

BACKGROUND

Modifying the shape and color of hair represents an important area of modern cosmetics. The consumer resorts to color-changing agents for fashionable hair style color schemes or for concealing gray or even white hair with fashionable or natural color tints.

For the provision of color-changing cosmetic agents, especially for the skin or keratin-containing fibers such as for example human hair, the person skilled in the art is aware of diverse systems according to the requirements of the dyeing or color modification.

The so-called oxidation dyes are used for long-lasting, intensive colorations with corresponding authentic characteristics. Such dyes usually comprise oxidation dye precursors, the "developer components" and "coupler components". Under the influence of oxidizing agents or from atmospheric oxygen, the developer components form the actual colorants among each other or by coupling with one or more coupler components. The oxidation dyes are distinguished by intensive, outstanding, long-lasting coloration results. However, for colorations with a natural appearance, a mixture of a large number of oxidation dye precursors can be employed; in many cases, further substantive dyes are used for nuancing.

In spite of their advantageous coloration properties, oxidative hair dyeing agents present disadvantages for the user. In particular, some of the common oxidation dye precursors, among them p-phenylenediamine, are suspected to cause irritations for some consumers and thereby sensitizations or even trigger allergic reactions. Consequently, for these substances there is still need for improvement in their physiological acceptance profile. In the search for replacement substances, many compounds have been studied but which suffer from application related problems, especially the lack of gray coverage capability. Moreover, in spite of the highly developed dyeing systems, there still exists the need for dyeing systems that achieve excellent luminance and intensity of the colorations, concomitant, however, providing a very good durability and an excellent homogeneity.

SUMMARY

Consequently, at least one object of the present invention is to reduce the abovementioned disadvantages of oxidative hair dyes. The dyes should produce intensive colorations with vivid colors and with a good resistance towards external influences, in particular with good fastness to light and to washing; also the colorations should suffer neither discoloration nor color shifts. Furthermore, the dyeing should exhibit the best possible levelling power and be unselective, i.e. achieve colorations that are as uniform and homogeneous as possible on differently pre-treated hair. Moreover, the dyes should have a toxicologically advantageous profile.

DETAILED DESCRIPTION

It has been found that certain cationic charged dimeric p-phenylenediamine derivatives are outstandingly suitable oxidation dye precursors for dyeing keratin-containing fibers. They produce colorations with a high color intensity and excellent brilliance as well as excellent gray coverage.

Cationic, dimeric substantive azo dyes for hair dyeing are known from FR 2864964. Dimers, uncharged dimeric p-phenylenediamines are known from EP 1 739 084 and EP 1 739 079 as developer components for oxidative hair dyes.

Up to now, cationically charged dimeric p-phenylenediamines corresponding to the Formula (I) below are unknown as oxidation dye precursors.

A first subject matter of the invention is therefore an agent for the oxidative color modification of keratinic fibers which is characterized in that it comprises in a cosmetic carrier at least one compound of the Formula (I) and/or its physiologically acceptable salt as the oxidation dye precursor of the developer type

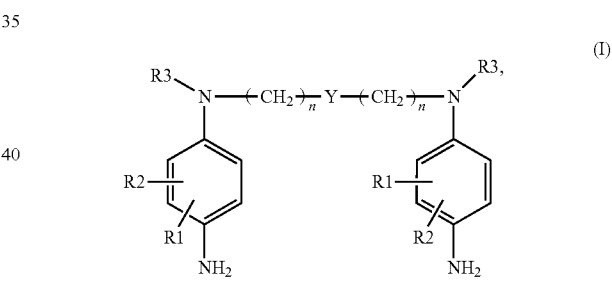

in which

R1 and R2 independently of one another stand for hydrogen, a $C_1$-$C_6$ alkyl group, a $C_2$-$C_6$ alkenyl group, a $C_1$-$C_6$ hydroxyalkyl group, a $C_2$-$C_6$ polyhydroxyalkyl group, a $C_1$-$C_6$ alkoxy group or a halogen atom, R3 stands for hydrogen, a $C_1$-$C_6$ alkyl group, a $C_2$-$C_6$ alkenyl group, a $C_2$-$C_6$ hydroxyalkyl group, a $C_2$-$C_6$ polyhydroxyalkyl group, a $C_1$-$C_6$ alkoxy $C_2$-$C_6$ alkyl group, a cyano-$C_1$-$C_6$ alkyl group or an aryl-$C_1$-$C_6$ alkyl group, n stands for a whole number from 2 to 6, Y stands for a cationic moiety of the Formulas (II) to (V),

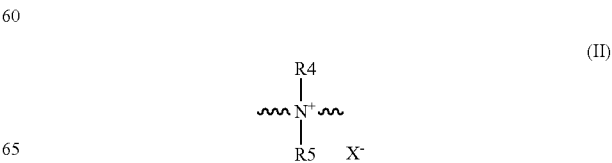

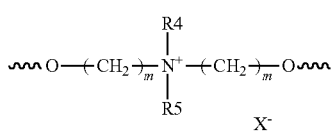

(III)

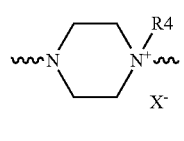

(IV)

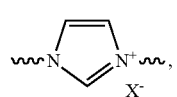

(V)

in which

R4, R5 stand independently of one another for a $C_1$-$C_6$ alkyl group, a $C_2$-$C_6$ alkenyl group, a $C_2$-$C_6$ hydroxyalkyl group, a polyhydroxy $C_2$-$C_6$ alkyl group, a $C_1$-$C_6$ alkoxy-$C_2$-$C_6$ alkyl group, a cyano-$C_1$-$C_6$ alkyl group, an aryl group or an aryl $C_1$-$C_6$ alkyl group, m stands for a whole number from 2 to 6 and $X^-$ stands for a physiologically acceptable anion.

Keratinic fibers are understood to mean wool, furs, feathers and especially human hair. However, the dyes according to the invention can, in principle, also be used for dyeing other natural fibers, such as e.g. cotton, jute, sisal, linen or silk, modified natural fibers, such as e.g. cellulose regenerate, nitrocellulose, alkyl cellulose or hydroxyalkyl cellulose or acetyl cellulose.

The inventive agents comprise the compounds of Formula (I) in a cosmetic carrier, preferably in a suitable aqueous, alcoholic or aqueous alcoholic carrier. For the purposes of dyeing hair, such carriers are, for example, creams, emulsions, gels or also surfactant-containing foaming solutions, such as, for example, shampoos, foam aerosols, foam formulations or other preparations that are suitable for use on the hair. However, it is also conceivable to integrate the dyestuff precursors of Formula (I) into a powdered or also tablet-shaped formulation.

In the context of the present invention, aqueous-alcoholic solutions are understood as meaning aqueous solutions comprising 3 to 70% by weight of a $C_1$-$C_4$ alcohol, in particular, ethanol or isopropanol. The compositions according to the invention can additionally comprise further organic solvents, such as, for example, methoxybutanol, benzyl alcohol, ethyl diglycol or 1,2-propylene glycol. Preference here is given to all water-soluble organic solvents.

Examples of the substituents R1, R2 as well as R3, R4, R5 and R6 cited in Formula (I) are cited below:

Exemplary $C_1$-$C_6$ alkyl groups are the groups —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$, —$(CH_2)_4CH_3$, —$(CH_2)_5CH_3$. Particularly preferred alkyl groups are methyl and ethyl. Exemplary $C_2$-$C_6$ alkenyl groups are prop-2-enyl (allyl group), 2-methyl-prop-2-enyl, but-3-enyl, but-2-enyl, pent-4-enyl or pent-3-enyl. Exemplary $C_1$-$C_6$ hydroxyalkyl groups are —$CH_2OH$, —$CH_2CH_2OH$, —$CH_2CH_2CH_2OH$, —$CH_2CH(OH)CH_3$ and —$CH_2CH_2CH_2CH_2OH$, the —$CH_2CH_2OH$ group being preferred. Examples of $C_2$-$C_6$ polyhydroxyalkyl groups are 2,3-dihydroxypropyl groups, 3,4-dihydroxybutyl groups, 2,4-dihydroxybutyl groups and 1,2-dihydroxyethyl groups. Examples of $C_1$-$C_6$ alkoxy groups are —$OCH_3$, —$OCH_2CH_3$, —$OCH_2CH_2CH_3$, —$OCH(CH_3)_2$ or —$OC(CH_3)_3$, preferably the methoxy group (—$OCH_3$). Exemplary $C_1$-$C_6$ alkoxy $C_2$-$C_6$ alkyl groups are —$CH_2OCH_3$, —$CH_2OCH_2CH_3$, —$CH_2CH_2OCH_3$, —$CH_2OCH(CH_3)_2$, —$CH_2CH_2OCH_3$, —$CH_2CH_2CH_2OCH_3$, —$CH_2CH_2OCH_2CH_3$, —$CH_2CH_2CH_2OCH_2CH_3$, —$CH_2CH_2OCH(CH_3)_2$, $CH_2CH_2CH_2OCH(CH_3)_2$. Examples of halogens are fluorine, chlorine, bromine or iodine, especially fluorine and chlorine. Examples of cyano-$C_1$-$C_6$ alkyl groups are —$CH_2CN$, —$C_2H_4CN$ and —$C_3H_6CN$. Examples of aryl-$C_1$-$C_6$ alkyl groups are benzyl, 1-phenylethyl and 2-phenylethyl.

In one embodiment of the first subject matter of the invention, an agent according to the invention is characterized in that it comprises at least one compound of the Formula (I), in which R1 and R2 independently of one another stand for hydrogen, a $C_1$-$C_6$ alkyl group, a $C_1$-$C_6$ alkoxy group or a halogen atom.

Another embodiment of the first subject matter of the invention is therefore characterized in that it comprises at least one compound of the Formula (I), in which R3 stands for hydrogen or a $C_1$-$C_6$ alkyl group, especially for hydrogen.

Particularly preferably, n stands for the number 2 or 3.

Another embodiment of the first subject matter of the invention is therefore characterized in that the agent comprises at least one compound of the Formula (I), in which R4 and R5 independently of one another stand for a $C_1$-$C_6$ alkyl group or a $C_2$-$C_6$ alkenyl group and/or m preferably stands for the number 2 or 3.

Particularly advantageous effects are achieved when Y stands for a cationic moiety of the Formulas (II) or (IV).

Another embodiment of the first subject matter of the invention is therefore characterized in that the agent comprises at least one compound of the Formula (I), in which Y stands for a cationic moiety of the Formulas (II) or (IV).

Particularly advantageous compounds are obtained when R1 and R2 independently of one another stand for hydrogen, a $C_1$-$C_6$ alkyl group, a $C_1$-$C_6$ alkoxy group or a halogen atom, R3 stands for hydrogen, n stands for 2 or 3, Y stands for a cationic moiety of the Formulas (II) or (IV) and R4 and R5 independently of one another stand for a $C_1$-$C_6$ alkyl group or a $C_2$-$C_6$ alkenyl group.

$X^-$ is a physiologically acceptable anion. $X^-$ is therefore preferably selected from chloride, sulfate, hydrogen sulfate, bromide, benzene sulfonate, p-toluene sulfone sulfonate, $C_1$-$C_4$ alkane sulfonate, $C_1$-$C_4$ alkane sulfate or trifluoromethane sulfonate as well as acetate, lactate, citrate, tartrate and/or the anionic salt fractions of other physiologically acceptable, organic acids.

Another embodiment of the first subject matter of the invention is therefore characterized in that the agent comprises at least one compound according to Formula (I), which is selected from the salts of

5

N,N-Dimethyl-3-[(4-aminophenyl)amino]-N-{3-[(4-aminophenyl)amino]propyl}-1-propanaminium

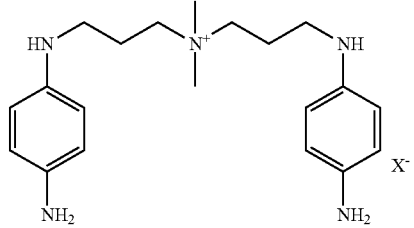

N-Ethyl-N-methyl-3-[(4-aminophenyl)amino]-N-{3-[(4-aminophenyl)amino]propyl}-1-propanaminium

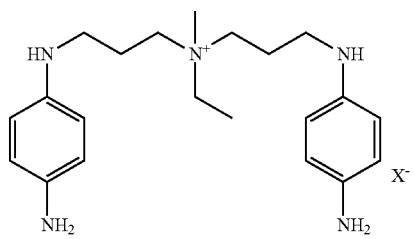

N-Methyl-N-propyl-3-[(4-aminophenyl)amino]-N-{3-[(4-aminophenyl)amino]propyl}-1-propanaminium

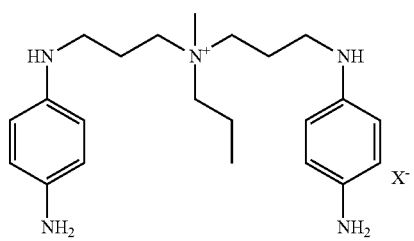

N-Allyl-N-methyl-3-[(4-aminophenyl)amino]-N-{3-[(4-aminophenyl)amino]-propyl}-1-propanaminium

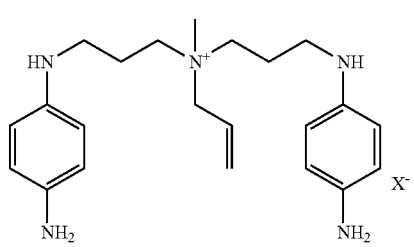

6

N,N-Dimethyl-2-[(4-aminophenyl)amino]-N-{2-[(4-aminophenyl)amino]ethyl}-1-ethanaminium

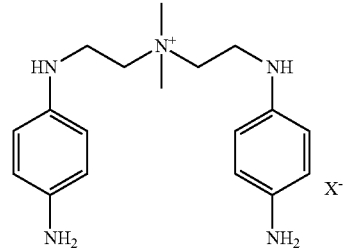

N-Ethyl-N-methyl-2-[(4-aminophenyl)amino]-N-{2-[(4-aminophenyl)amino]ethyl}-1-ethanaminium

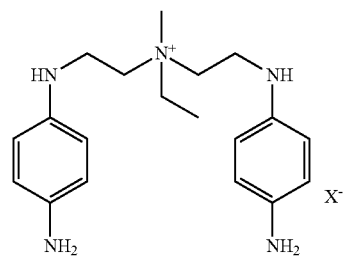

N-Methyl-N-propyl-2-[(4-aminophenyl)amino]-N-{2-[(4-aminophenyl)amino]ethyl}-1-ethanaminium

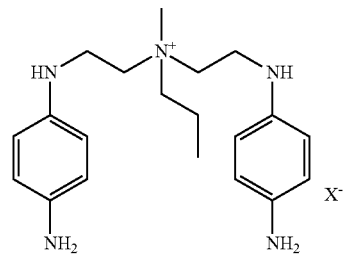

N-Allyl-N-methyl-2-[(4-aminophenyl)amino]-N-{2-[(4-aminophenyl)amino]ethyl}-1-ethanaminium

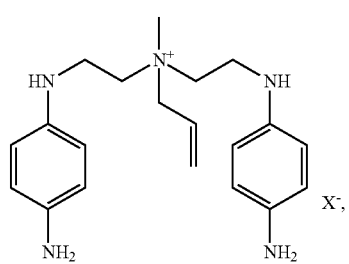

| 7 | 8 |
|---|---|
| N1,N4-Bis-{3-[(4-aminophenyl)amino]propyl}-N1-methylpiperazinium | N1,N4-Bis-{3-[(4-aminophenyl)amino]propyl}-N1-allylpiperazinium |

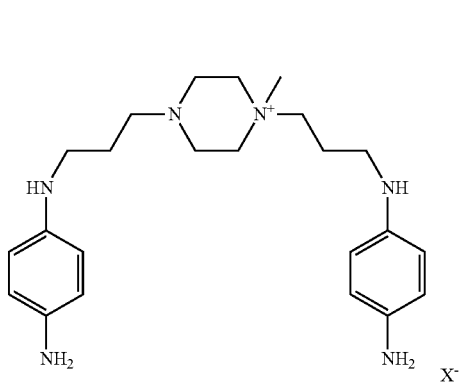 [SMILES: C[N+]1(CCCNc2ccc(N)cc2)CCN(CCCNc2ccc(N)cc2)CC1 ; "X-"]

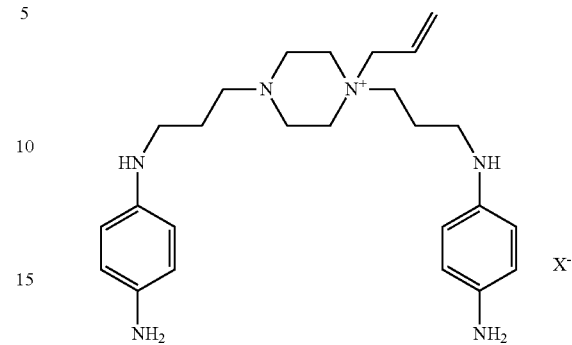

N1,N4-Bis-{2-[(4-aminophenyl)amino]ethyl}-N1-methylpiperazinium

N1,N4-Bis-{3-[(4-aminophenyl)amino]propyl}-N1-ethylpiperazinium

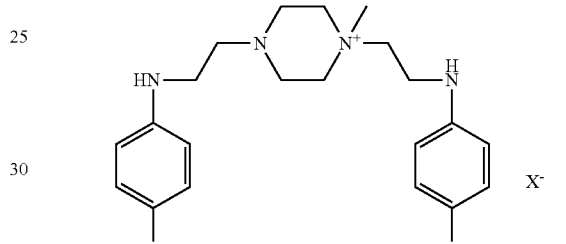

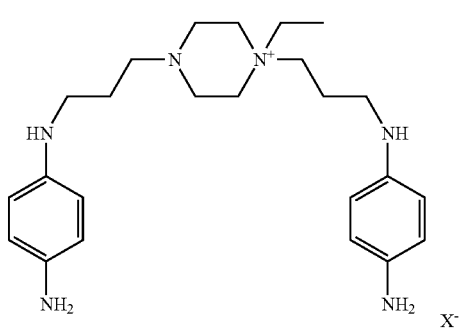 [SMILES: CC[N+]1(CCCNc2ccc(N)cc2)CCN(CCCNc2ccc(N)cc2)CC1 ; "X-"]

N1,N4-Bis-{2-[(4-aminophenyl)amino]ethyl}-N1-ethylpiperazinium

N1,N4-Bis-{3-[(4-aminophenyl)amino]propyl}-N1-propylpiperazinium

N1,N4-Bis-{2-[(4-aminophenyl)amino]ethyl}-N1-propylpiperazinium

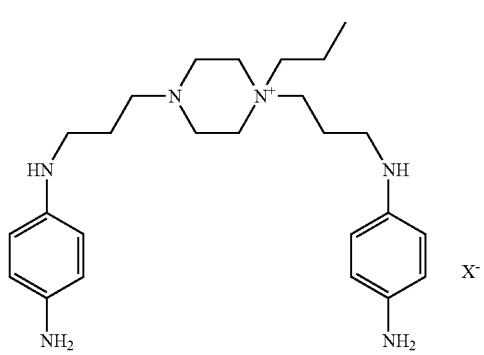

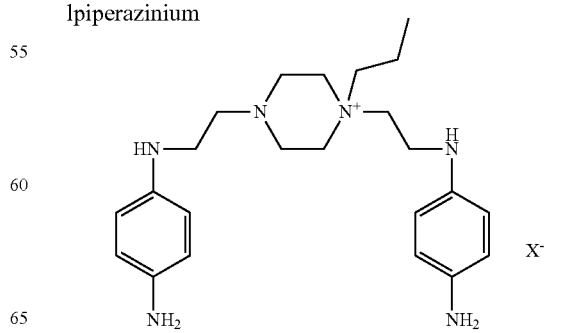

N1,N4-Bis-{2-[(4-aminophenyl)amino]ethyl}-N1-allylpiperazinium

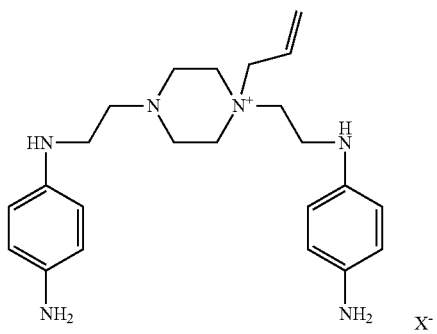 [SMILES: C=CC[N+]1(CCNc2ccc(N)cc2)CCN(CCNc2ccc(N)cc2)CC1 ; "X-"]

N,N-Dimethyl-3-[(4-amino-3-methylphenyl)amino]-N-{3-[(4-amino-3-methylphenyl)amino]propyl}-1-propanaminium

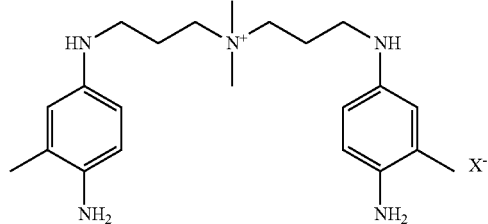

N-Ethyl-N-methyl-3-[(4-amino-3-methylphenyl)amino]-N-{3-[(4-amino-3-methylphenyl)amino]propyl}-1-propanaminium

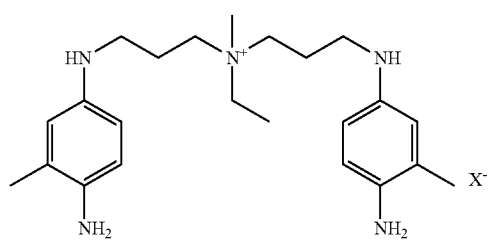

N-Methyl-N-propyl-3-[(4-amino-3-methylphenyl)amino]-N-{3-[(4-amino-3-methylphenyl)amino]propyl}-1-propanaminium

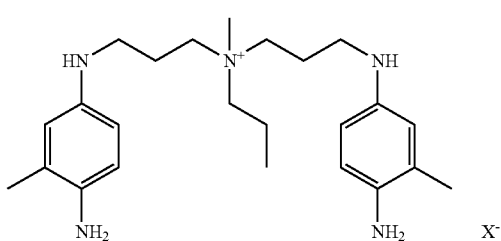

N-Allyl-N-methyl-3-[(4-amino-3-methylphenyl)amino]-N-{3-[(4-amino-3-methylphenyl)amino]propyl}-1-propanaminium

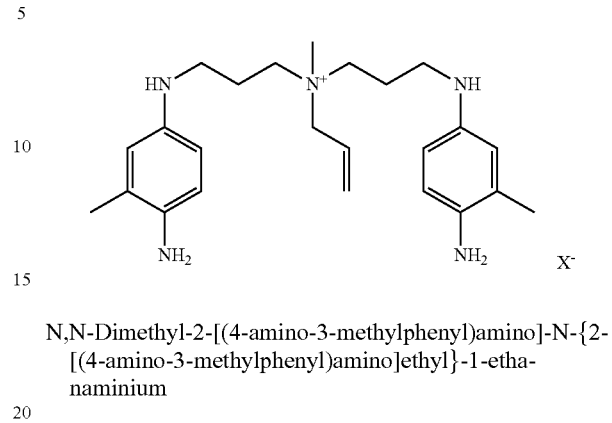

N,N-Dimethyl-2-[(4-amino-3-methylphenyl)amino]-N-{2-[(4-amino-3-methylphenyl)amino]ethyl}-1-ethanaminium

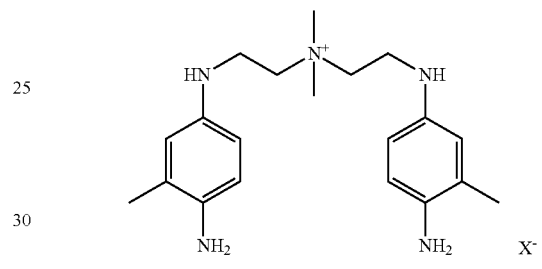

N-Ethyl-N-methyl-2-[(4-amino-3-methylphenyl)amino]-N-{2-[(4-amino-3-methylphenyl)amino]-ethyl}-1-ethanaminium

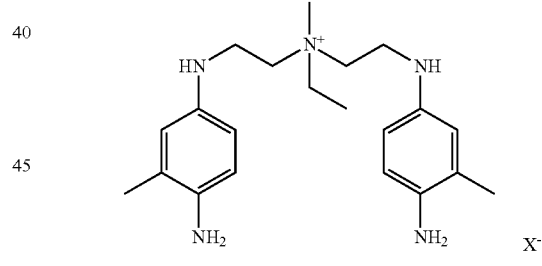

N-Methyl-N-propyl-2-[(4-amino-3-methylphenyl)amino]-N-{2-[(4-amino-3-methylphenyl)-amino]ethyl}-1-ethanaminium

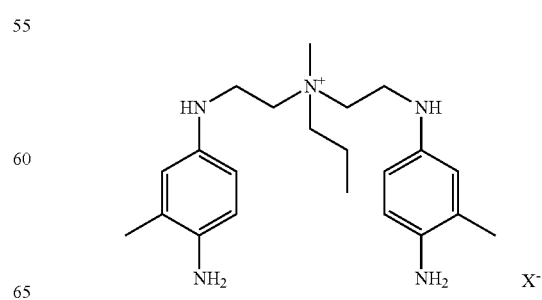

N-Allyl-N-methyl-2-[(4-amino-3-methylphenyl)amino]-N-{2-[(4-amino-3-methylphenyl)amino]-ethyl}-1-ethanaminium N-Allyl-N-methyl-3-[(4-amino-3-methoxyphenyl)amino]-N-{3-[(4-amino-3-methoxyphenyl)-amino]propyl}-1-propanaminium

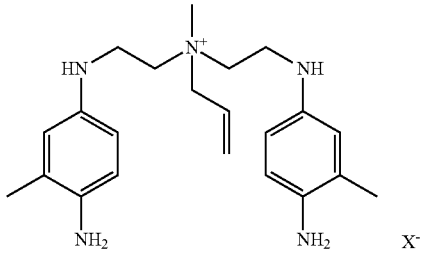

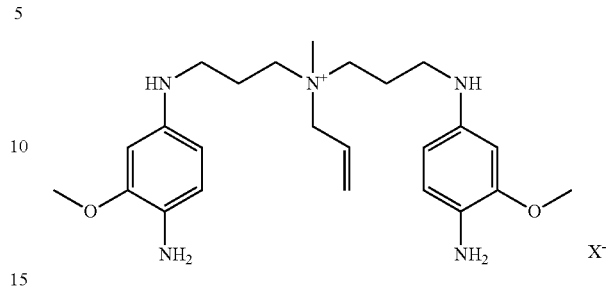

N,N-Dimethyl-3-[(4-amino-3-methoxyphenyl)amino]-N-{3-[(4-amino-3-methoxyphenyl)amino]-propyl}-1-propanaminium N,N-Dimethyl-2-[(4-amino-3-methoxyphenyl)amino]-N-{2-[(4-amino-3-methoxyphenyl)-amino]ethyl}-1-ethanaminium

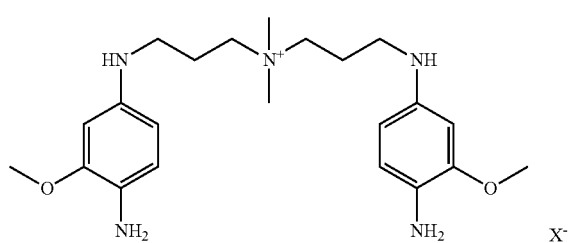

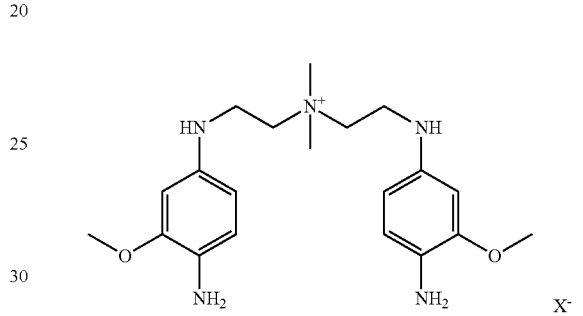

N-Ethyl-N-methyl-3-[(4-amino-3-methoxyphenyl)amino]-N-{3-[(4-amino-3-methoxyphenyl)amino]propyl}-1-propanaminium N-Ethyl-N-methyl-2-[(4-amino-3-methoxyphenyl)amino]-N-{2-[(4-amino-3-methoxyphenyl)-amino]ethyl}-1-ethanaminium

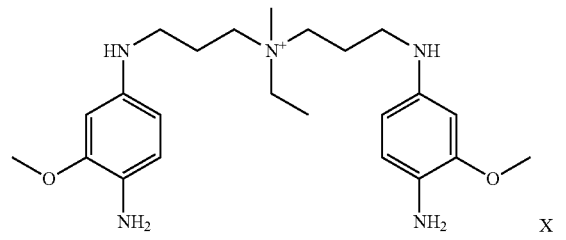

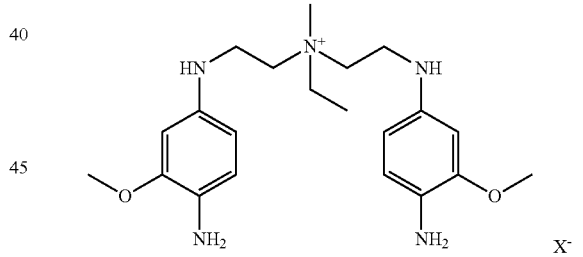

N-Methyl-N-propyl-3-[(4-amino-3-methoxyphenyl)amino]-N-{3-[(4-amino-3-methoxyphenyl)-amino]propyl}-1-propanaminium N-Methyl-N-propyl-2-[(4-amino-3-methoxyphenyl)amino]-N-{2-[(4-amino-3-methoxyphenyl)amino]ethyl}-1-ethanaminium

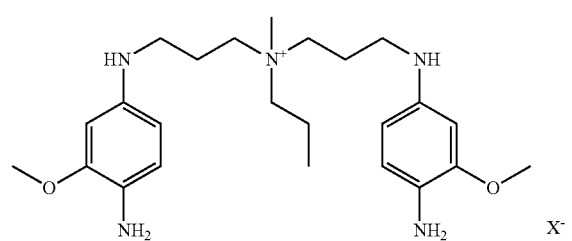

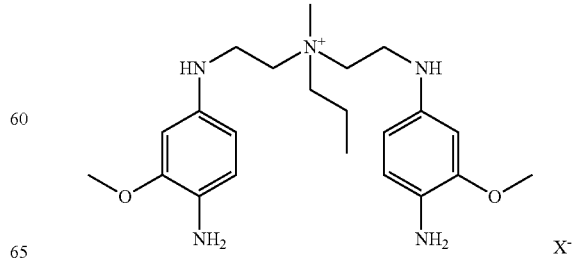

N-Allyl-N-methyl-2-[(4-amino-3-methoxyphenyl)amino]-N-{2-[(4-amino-3-methoxyphenyl)amino]ethyl}-1-ethanaminium

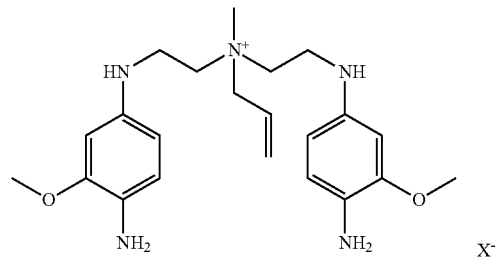

X⁻

N-Allyl-N-methyl-3-[(4-amino-3-chlorophenyl)amino]-N-{3-[(4-amino-3-chlorophenyl)amino]-propyl}-1-propanaminium

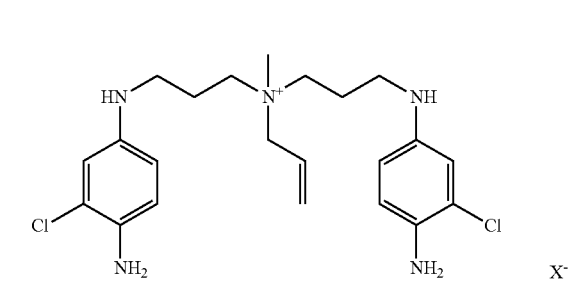

X⁻

N,N-Dimethyl-3-[(4-amino-3-chlorophenyl)amino]-N-{3-[(4-amino-3-chlorophenyl)amino]propyl}-1-propanaminium

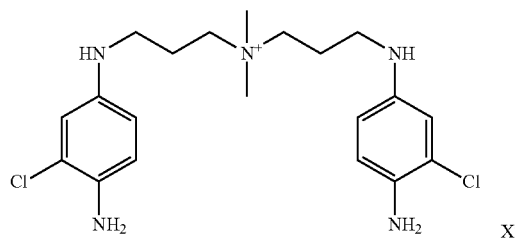

X⁻

N,N-Dimethyl-2-[(4-amino-3-chlorophenyl)amino]-N-{2-[(4-amino-3-chlorophenyl)amino]ethyl}-1-ethanaminium

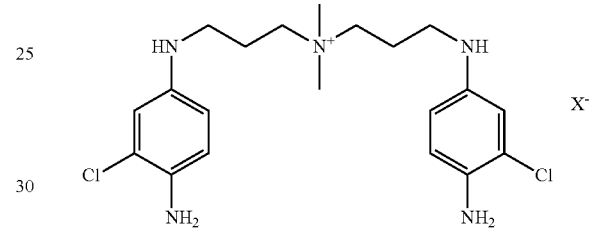

X⁻

N-Ethyl-N-methyl-3-[(4-amino-3-chlorophenyl)amino]-N-{3-[4-amino-3-chlorophenyl)amino]-propyl}-1-propanaminium

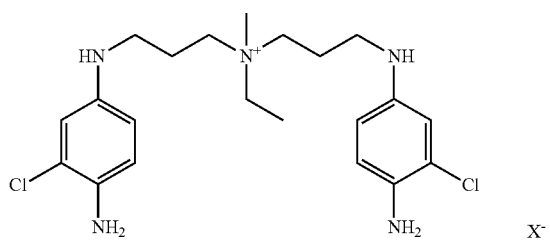 [SMILES: CC[N+](C)(CCCNc1ccc(N)c(Cl)c1)CCCNc1ccc(N)c(Cl)c1 ; "X-"]

X⁻

N-Ethyl-N-methyl-2-[(4-amino-3-chlorophenyl)amino]-N-{2-[(4-amino-3-chlorophenyl)amino]-ethyl}-1-ethanaminium

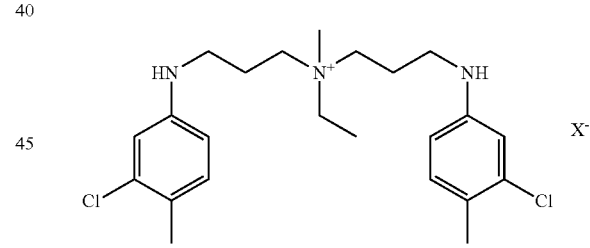

X⁻

N-Methyl-N-propyl-3-[(4-amino-3-chlorophenyl)amino]-N-{3-[(4-amino-3-chlorophenyl)amino]-propyl}-1-propanaminium

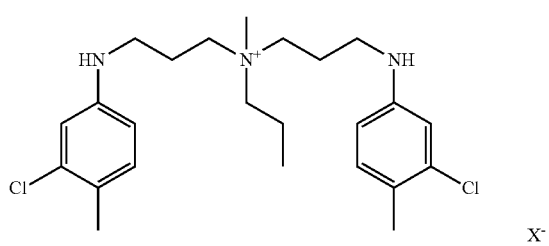 [SMILES: CCC[N+](C)(CCCNc1ccc(C)c(Cl)c1)CCCNc1ccc(C)c(Cl)c1 ; "X-"]

X⁻

N-Methyl-N-propyl-2-[(4-amino-3-chlorophenyl)amino]-N-{2-[(4-amino-3-chlorophenyl)amino]-ethyl}-1-ethanaminium

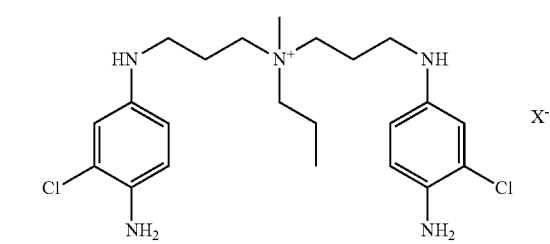 [SMILES: CCC[N+](C)(CCCNc1ccc(N)c(Cl)c1)CCCNc1ccc(N)c(Cl)c1 ; "X-"]

X⁻

Salts of N-Allyl-N-methyl-2-[(4-amino-3-chlorophenyl)amino]-N-{2-[(4-amino-3-chlorophenyl)amino]ethyl}-1-ethanaminium

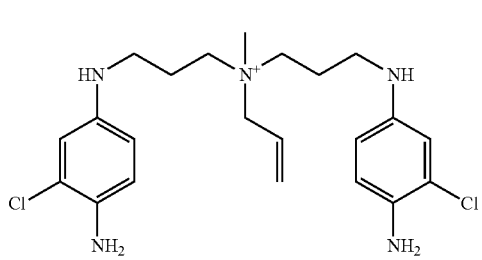

of N,N-Dimethyl-3-[(4-amino-2-methylphenyl)amino]-N-{3-[(4-amino-2-methylphenyl)amino]-propyl}-1-propanaminium

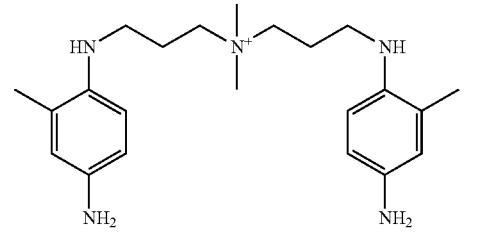

of N-Ethyl-N-methyl-3-[(4-amino-2-methylphenyl)amino]-N-{3-[(4-amino-2-methylphenyl)amino]-propyl}-1-propanaminium

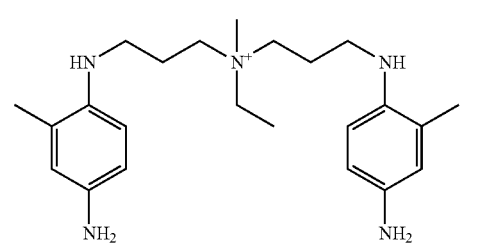

of N-Methyl-N-propyl-3-[(4-amino-2-methylphenyl)amino]-N-{3-[(4-amino-2-methylphenyl)amino]propyl}-1-propanaminium

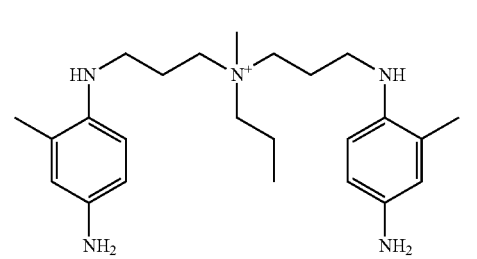

of N-Allyl-N-methyl-3-[(4-amino-2-methylphenyl)amino]-N-{3-[(4-amino-2-methylphenyl)amino]-propyl}-1-propanaminium

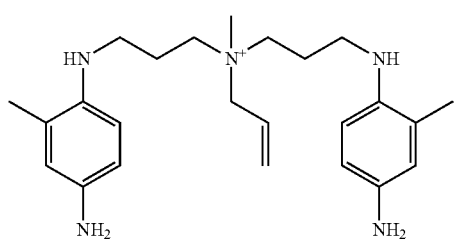

of N1,N4-Bis-{3-[(4-amino-3-methylphenyl)amino]propyl}-N1-methylpiperazinium

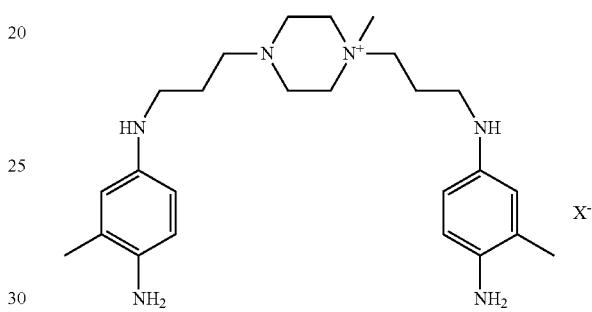

of N1,N4-Bis-{3-[(4-amino-3-methylphenyl)amino]propyl}-N1-ethylpiperazinium

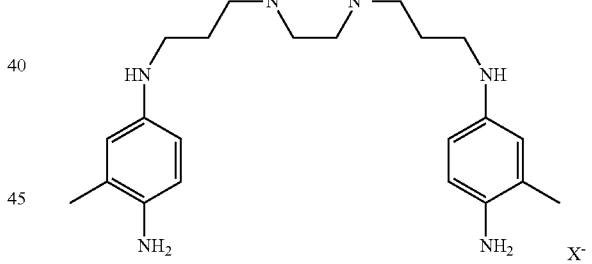

of N1,N4-Bis-{3-[(4-amino-3-methylphenyl)amino]propyl}-N1-propylpiperazinium

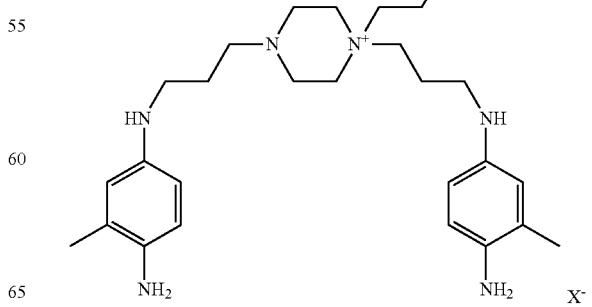

of N1,N4-Bis-{3-[(4-amino-3-methylphenyl)amino]propyl}-N1-allylpiperazinium

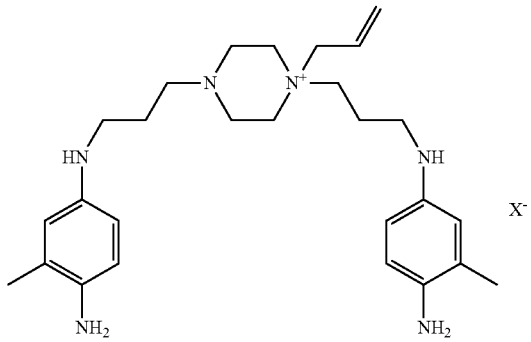

of N1,N4-Bis-{2-[(4-amino-3-methylphenyl)amino]ethyl}-N1-methylpiperazinium

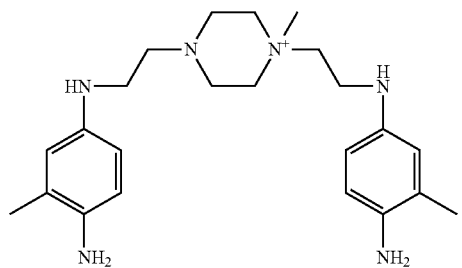

of N1,N4-Bis-{2-[(4-amino-3-methylphenyl)amino]ethyl}-N1-ethylpiperazinium

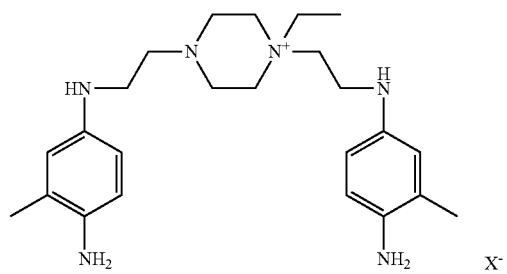

of N1,N4-Bis-{2-[(4-amino-3-methylphenyl)amino]ethyl}-N1-propylpiperazinium

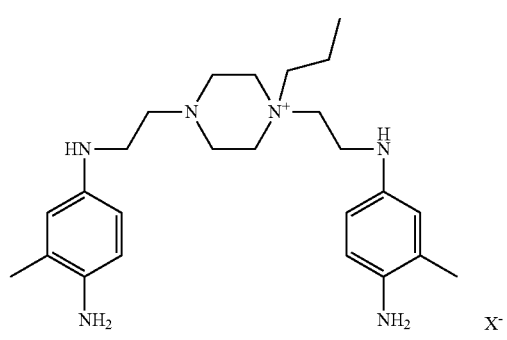

of N1,N4-Bis-{2-[(4-amino-3-methylphenyl)amino]ethyl}-N1-allylpiperazinium

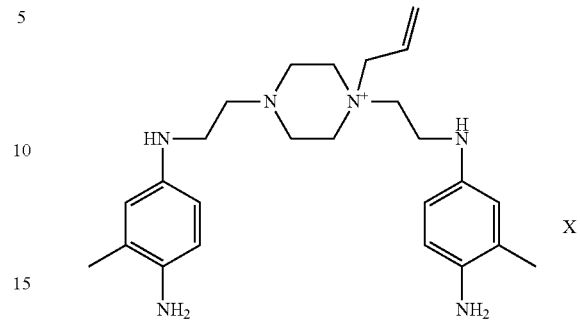

Another embodiment of the first subject matter of the invention is therefore characterized in that the agent comprises at least one compound according to Formula (I), which is selected from the salts of N,N-Dimethyl-3-[(4-aminophenyl)amino]-N-{3-[(4-aminophenyl)amino]propyl}-1-propanaminium N-Ethyl-N-methyl-3-[(4-aminophenyl)amino]-N-{3-[(4-aminophenyl)amino]propyl}-1-propanaminium N-Methyl-N-propyl-3-[(4-aminophenyl)amino]-N-{3-[(4-aminophenyl)amino]-propyl}-1-propanaminium N-Allyl-N-methyl-3-[(4-aminophenyl)amino]-N-{3-[(4-aminophenyl)amino]-propyl}-1-propanaminium N1,N4-Bis-{3-[(4-aminophenyl)amino]propyl}-N1-methylpiperazinium N1,N4-Bis-{2-[(4-aminophenyl)amino]ethyl}-N1-methylpiperazinium N,N-Dimethyl-3-[(4-amino-3-methylphenyl)amino]-N-{3-[(4-amino-3-methylphenyl)amino]propyl}-1-propanaminium N-Ethyl-N-methyl-3-[(4-amino-3-methylphenyl)amino]-N-{3-[(4-amino-3-methylphenyl)amino]propyl}-1-propanaminium N-Methyl-N-propyl-3-[(4-amino-3-methylphenyl)amino]-N-{3-[(4-amino-3-methylphenyl)amino]propyl}-1-propanaminium N,N-Dimethyl-3-[(4-amino-2-methylphenyl)amino]-N-{3-[(4-amino-2-methylphenyl)amino]propyl}-1-propanaminium N-Ethyl-N-methyl-3-[(4-amino-2-methylphenyl)amino]-N-{3-[(4-amino-2-methylphenyl)amino]propyl}-1-propanaminium N-Methyl-N-propyl-3-[(4-amino-2-methylphenyl)amino]-N-{3-[(4-amino-2-methylphenyl)amino]propyl}-1-propanaminium N1,N4-Bis-{3-[(4-amino-3-methylphenyl)amino]propyl}-N1-methylpiperazinium N1,N4-Bis-{2-[(4-amino-3-methylphenyl)amino]ethyl}-N1-methylpiperazinium.

The compounds of the Formula (I) can be employed in the form of their physiologically acceptable salts, especially the chlorides, the sulfates and bromides. Further preferred salts are derived from sulfonic acids, such as benzene sulfonates, p-toluene sulfonates, $C_1$-$C_4$ alkane sulfonates or trifluoromethane sulfonates. Depending on the number of amino groups comprised in the compounds according to the invention, mono, di, tri, tetra and higher adducts can be present as the salts.

Inventively preferred agents are characterized in that they comprise the compounds of the Formula (I) and/or their physiologically acceptable salts in a quantity by weight of about 0.001 to about 10 wt %, in particular about 0.05 to about 5 wt %, based on the total weight of the ready for use agent.

The compounds of the Formula (I) can be comprised as the sole color modifying compounds in the inventive agent. However, it is inventively preferred if the agent additionally comprises an oxidation dye precursor of the coupler component type.

Coupler components alone, in the context of the oxidative dyeing, do not form any significant coloration; rather they always need the presence of developer components.

In the context of the invention, coupler components allow at least one substitution of a chemical group of the coupler by the oxidized form of the developer component. For this, covalent bonds are formed between coupler components and developer components.

At least one compound from one of the following classes is preferably selected as the inventively suitable coupler component:
- m-Aminophenol and/or its derivatives,
- m-Diaminobenzene and/or its derivatives,
- o-Diaminobenzene and/or its derivatives,
- o-Aminophenol derivatives, such as for example o-aminophenol,
- Naphthalene derivatives with at least one hydroxy group,
- Di or trihydroxybenzene and/or their derivatives,
- Pyridine derivatives,
- Pyrimidine derivatives,
- Monohydroxyindole derivatives and/or monoaminoindole derivatives,
- Monohydroxyindoline derivatives and/or monoaminoindoline derivatives,
- Pyrazolone derivatives, such as for example 1-phenyl-3-methylpyrazol-5-one,
- Morpholine derivatives such as, for example 6-hydroxybenzomorpholine or 6-aminobenzomorpholine,
- Quinoxaline derivatives such as, for example, 6-methyl-1,2,3,4-tetrahydroquinoxaline.

Mixtures of two or more compounds from one or more of these classes are likewise inventive in the context of this embodiment.

According to the invention, particularly preferred coupler components are selected from 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, 3-phenylenediamine, 2-(2,4-diaminophenoxy)-ethanol, 1,3-bis(2,4-diaminophenoxy)propane, 1-methoxy-2-amino-4-(2-hydroxyethylamino)-benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline or mixtures of these compounds or the physiologically acceptable salts of the aforementioned compounds. In this regard, resorcinol, 2-methylresorcinol, 5-amino-2-methylphenol, 3-aminophenol, 2-(2,4-diaminophenoxy)ethanol, 1,3-bis(2,4-diaminophenoxy)propane, 1-methoxy-2-amino-4-(2'-hydroxyethylamino)benzene, 2-amino-3-hydroxypyridine and 1-naphthol as well as their physiologically acceptable salts are quite particularly preferred.

The coupler components are preferably used in an amount of about 0.0001 to about 10 wt %, preferably about 0.01 to about 5.0 wt %, in each case based on the ready-for-use agent.

The following combinations of an inventive developer with selected couplers are particularly advantageous in this respect:

N,N-dimethyl-3-[(4-aminophenyl)amino]-N-{3-[(4-aminophenyl)amino]propyl}-1-propanaminium p-toluene sulfonate, tetrahydrochloride and one or more compounds, selected from 5-amino-2-methylphenol, 3-amino-2-chloro-6-methylphenol, 2,4-dichloro-3-aminophenol, 2-(2,4-diaminophenoxy)ethanol, 1,3-bis(2,4-diaminophenoxy)propane, resorcinol, 2-methylresorcinol, 2-amino-3-hydroxypyridine, 3-amino-2-methylamino-6-methoxypyridine, 1-naphthol, 1,5-dihydroxynaphthalene, 2,7-dihydroxynaphthalene.

N-ethyl-N-methyl-3-[(4-aminophenyl)amino]-N-{3-[(4-aminophenyl)amino]propyl}-1-propanaminium p-toluene sulfonate, tetrahydrochloride and one or more compounds, selected from 5-amino-2-methylphenol, 3-amino-2-chloro-6-methylphenol, 2,4-dichloro-3-aminophenol, 2-(2,4-diaminophenoxy)ethanol, 1,3-bis(2,4-diaminophenoxy)propane, resorcinol, 2-methylresorcinol, 2-amino-3-hydroxypyridine, 3-amino-2-methylamino-6-methoxypyridine, 1-naphthol, 1,5-dihydroxynaphthalene, 2,7-dihydroxynaphthalene.

N-methyl-N-propyl-3-[(4-aminophenyl)amino]-N-{3-[(4-aminophenyl)amino]propyl}-1-propanaminium p-toluene sulfonate, tetrahydrochloride one or more compounds, selected from 5-amino-2-methylphenol, 3-amino-2-chloro-6-methylphenol, 2,4-dichloro-3-aminophenol, 2-(2,4-diaminophenoxy)ethanol, 1,3-bis(2,4-diaminophenoxy)propane, resorcinol, 2-methylresorcinol, 2-amino-3-hydroxypyridine, 3-amino-2-methylamino-6-methoxypyridine, 1-naphthol, 1,5-dihydroxynaphthalene, 2,7-dihydroxynaphthalene.

N1,N4-bis-{3-[(4-aminophenyl)amino]propyl}-N1-methylpiperazinium p-toluene sulfonate, hydrochloride and one or more compounds, selected from 5-amino-2-methylphenol, 3-amino-2-chloro-6-methylphenol, 2,4-dichloro-3-aminophenol, 2-(2,4-diaminophenoxy)ethanol, 1,3-bis(2,4-diaminophenoxy)propane, resorcinol, 2-methylresorcinol, 2-amino-3-hydroxypyridine, 3-amino-2-methylamino-6-methoxypyridine, 1-naphthol, 1,5-dihydroxynaphthalene, 2,7-dihydroxynaphthalene.

N,N-dimethyl-3-[(4-amino-3-methylphenyl)amino]-N-{3-[(4-amino-3-methylphenyl)amino]propyl}-1-propanaminium p-toluene sulfonate, tetrahydrochloride and one or more compounds, selected from 5-amino-2-methylphenol, 3-amino-2-chloro-6-methylphenol, 2,4-dichloro-3-aminophenol, 2-(2,4-diaminophenoxy)ethanol, 1,3-bis(2,4-diaminophenoxy)propane, resorcinol, 2-methylresorcinol, 2-amino-3-hydroxypyridine, 3-amino-2-methylamino-6-methoxypyridine, 1-naphthol, 1,5-dihydroxynaphthalene, 2,7-dihydroxynaphthalene.

N-ethyl-N-methyl-3-[(4-amino-3-methylphenyl)amino]-N-{3-[(4-amino-3-methylphenyl)amino]-propyl}-1-propanaminium p-toluene sulfonate, tetrahydrochloride and one or more compounds, selected from 5-amino-2-methylphenol, 3-amino-2-chloro-6-methylphenol, 2,4-dichloro-3-aminophenol, 2-(2,4-diaminophenoxy)ethanol, 1,3-bis(2,4-diaminophenoxy)propane, resorcinol, 2-methylresorcinol, 2-amino-3-hydroxypyridine, 3-amino-2-methylamino-6-methoxypyridine, 1-naphthol, 1,5-dihydroxynaphthalene, 2,7-dihydroxynaphthalene.

N-methyl-N-propyl-3-[(4-amino-3-methylphenyl)amino]-N-{3-[(4-amino-3-methylphenyl)amino]propyl}-1-propanaminium p-toluene sulfonate, tetrahydrochloride and one or more compounds, selected from 5-amino-2-methylphenol, 3-amino-2-chloro-6-methylphenol, 2,4-dichloro-3-aminophenol, 2-(2,4-diaminophenoxy)ethanol, 1,3-bis(2,4-diaminophenoxy)propane, resorcinol, 2-methylresorcinol, 2-amino-3-hydroxypyridine, 3-amino-2-methylamino-6-methoxypyridine, 1-naphthol, 1,5-dihydroxynaphthalene, 2,7-dihydroxynaphthalene.

In order to achieve a balanced and subtle development of nuances, it is inventively advantageous for additional chromophoric components to be comprised in the agent according to the invention.

It can therefore be inventively preferred for the agent to comprise at least one additional chromophoric component that is selected from further oxidation dye precursors of the developer type and/or substantive dyes.

In addition to the oxidation dye precursors of the developer type according to Formula (I), the inventive agents can additionally comprise at least one further developer component.

Preferred additional developer components are selected from at least one compound from the group consisting of p-phenylenediamine, p-toluoylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diamino-2-propanol, bis-(2-hydroxy-5-aminophenyl)methane, 1,3-bis-(2,5-diaminophenoxy)-2-propanol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol and 4-amino-2-(diethylaminomethyl)phenol, 4,5-diamino-1-(2-hydroxyethyl)pyrazole, 2,4,5,6-tetraminopyrimidine, 4-hydroxy-2,5,6-triaminopyrimidine, 2-hydroxy-4,5,6-triaminopyrimidine, as well as the physiologically acceptable salts of these compounds. Particularly preferred developer components in this regard are p-toluoylenediamine, 2-(2-hydroxyethyl)-p-phenylenediamine, 2-methoxymethyl-p-phenylenediamine, N-(4-amino-3-methylphenyl)-N-[3-(1H-imidazol-1-yl)propyl]amine, and/or 4,5-diamino-1-(2-hydroxyethyl)pyrazole as well as their physiologically acceptable salts.

The additional developer components are preferably used in an amount of about 0.0001 to about 10 wt %, preferably about 0.001 to about 5 wt %, in each case based on the ready-for-use agent.

The inventive agents can further comprise at least one substantive dye. These are dyes that are directly absorbed onto the hair and do not require any oxidative process to develop the color. Substantive dyes are usually nitrophenylenediamines, nitroaminophenols, azo dyes, anthraquinones or indophenols.

The substantive dyes are preferably employed in quantities of about 0.001 to about 20 wt %, in particular about 0.05 to about 5 wt %, each based on the total end-use preparation. The total amount of substantive dyes is preferably about 3 wt % at most.

Substantive dyes can be subdivided into anionic, cationic and non-ionic substantive dyes which based on the requirements of the carrier are selected and employed by the person skilled in the art.

Preferred anionic substantive dyestuffs are known compounds with the international designations or trade names Bromophenol blue, Tetrabromophenol blue, Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1 and Acid Black 52.

Preferred cationic substantive dyestuffs are Basic Blue 7, Basic Blue 26, Basic Violet 2 and Basic Violet 14, Basic Yellow 57, Basic Red 76, Basic Blue 16, Basic Blue 347 (Cationic Blue 347/Dystar), Basic Blue 99, Basic Brown 16 and Basic Brown 17 as well as Yellow 87, Basic Orange 31 and Basic Red 51.

Non-ionic nitro and quinone dyes and neutral azo dyes are particularly suitable as non-ionic substantive dyes. Preferred non-ionic substantive dyes are the compounds known under the international designations or trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzene, 2-amino-4-nitrophenol, 1,4-bis-(2-hydroxyethyl)-amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-Amino-2-nitrophenyl)amino]-benzoic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethylamino-4-nitrophenol.

It is not required that each of the optionally comprised substantive dyestuffs be pure compounds. In fact, due to the manufacturing processes for the individual dyes, minor quantities of even more components may be comprised, in so far as they have no detrimental influence on the coloration result or that they must be excluded on other grounds, e.g. toxicological.

In addition to the compound according to Formula (II) the inventive agents can also comprise dyes that are analogous to nature. Preparations according to the invention which comprise precursors of nature-analogous dyes are preferably used as the atmospherically oxidative colorant. In this embodiment, an additional oxidizing agent is consequently not added to the cited compositions.

The dye precursors of nature-analogous dyes are each preferably employed in a quantity of about 0.001 to about 5 wt %, based on the total end-use preparation. Derivatives of 5,6-dihydroxyindoline, in particular 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline as well as 5,6-dihydroxyindoline-2-carboxylic acid, as well as other derivatives of 5,6-dihydroxyindole, in particular 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, 5,6-dihydroxyindole-2-carboxylic acid, as well as physiologically acceptable salts of the abovementioned compounds are suitable as particularly good precursors of nature-analogous hair dyes.

In the case of the oxidative dyeing, the color development can in principle occur with atmospheric oxygen. However, it is preferred to use a chemical oxidizing agent, particularly when a lightening effect on human hair is desired in addition to the dyeing. This lightening effect may be desired independently of the dyeing method. Persulfates, peroxodisulfates, chlorites, hypochlorites and particularly hydrogen peroxide or and/or one of its solid addition products on organic or inorganic compounds can be used as the oxidizing agent.

In order to prevent a premature, unwanted reaction of the oxidation dye precursors with the oxidizing agent, the oxidation dye precursors and the oxidizing agent itself are advantageously packaged separately from one another and first brought into contact directly prior to use.

In another embodiment of the present invention, agents are therefore preferred that are characterized in that they are produced by blending at least two preparations directly prior to use, wherein the at least two preparations are provided in at least two separately packaged containers, and wherein one container comprises a dye (A) that comprises in a cosmetic carrier at least one oxidation dye precursor according to Formula (I), and an additional container that comprises an oxidizing agent preparation (B), comprising at least one oxidizing agent.

The oxidizing agent preparation (B) comprises hydrogen peroxide and/or one of its solid addition products on organic or inorganic compounds, such as urea, melamine and sodium borate as the oxidizing agent.

The quantity of oxidizing agent in the ready-to-use agent is preferably about 0.5 to about 12 wt %, preferably about 2 to about 10 wt %, particularly preferably about 3 to about 6 wt % (calculated as 100% conc. $H_2O_2$), each based on the ready-for-use agent.

Such oxidizing agent preparations are preferably aqueous, free-flowing oxidizing agent preparations. In this regard, preferred preparations are characterized in that the free-flowing oxidizing agent preparation—based on its weight—comprises about 40 to about 90 wt %, preferably about 50 to about 85 wt %, particularly preferably about 55 to about 80 wt % more preferably about 60 to about 77.5 wt. % and particularly about 65 to about 75 wt. % water.

According to the invention, however, the oxidation dyeing composition can also be applied to the hair together with a catalyst that activates the oxidation of the dye precursors. Such catalysts are e.g. certain enzymes, iodides, quinones or metal ions.

In addition it has proven advantageous when the oxidizing agent preparations comprise at least one stabilizer or complexant. Common and in the context of the present invention preferred complexants and stabilizers are for example polyoxycarboxylic acids, polyamines, ethylenediamine tetraacetic acid (EDTA), N-hydroxyethylethylenediamine triacetic acid, diethylenetriamine pentaacetic acid (DTPA), ethylenediamine disuccinic acid (EDDS), hydroxyethylimino diacetic acid, nitridodiacetic acid-3-propionic acid, isoserine diacetic acid, N,N-di-(2-hydroxyethyl)glycine, N-(1,2-dicarboxy-2-hydroxyethyl)glycine, N-(1,2-dicarboxy-2-hydroxyethyl)aspartic acid or nitrilotriacetic acid (NTA), ethylenediamine diglutaric acid (EDGA), 2-hydroxypropylenediamine disuccinic acid (HPDS), glycinamide-N,N'-disuccinic acid (GADS), ethylenediamine-N—N'-diglutaric acid (EDDG), 2-hydroxypropylenediamine-N—N'-disuccinic acid (HP-DDS), diaminoalkyldi-(sulfosuccinic acid) (DDS), ethylenedicysteic acid (EDC), ethylenediamine-N—N'-bis(ortho-hydroxyphenyl)acetic acid (EDDHA), N-2-hydroxyethylamine-N,N-diacetic acid, glycerylimino diacetic acid, imino diacetic acid-N-2-hydroxy-propylsulfonic acid, aspartic acid-N-carboxymethyl-N-2,5-hydroxypropyl-3-sulfonic acid, β-alanine-N,N'-diacetic acid, aspartic acid-N,N'-diacetic acid, aspartic acid-N-monoacetic acid, dipicolinic acid, as well as their salts and/or derivatives, geminal diphosphonic acids such as 1-hydroxyethane-1,1-diphosphonic acid (HEDP), their higher homologs with up to 8 carbon atoms as well as hydroxy- or amino group-containing derivatives thereof and 1-aminoethane-1,1-diphosphonic acid, its higher homologs with up to 8 carbon atoms as well as hydroxy- or amino group-containing derivatives, amino phosphonic acids such as ethylenediaminetetra(methylenephosphonic acid) (EDTMP), diethylenetriamine penta(methylenephosphonic acid) (DTPMP) as well as their higher homologs, or nitrilo tri(methylenephosphonic acid), phosphonopolycarboxylic acids such as 2-phosphonobutane-1,2,4-tricarboxylic acid, cyclodextrins, as well as alkali metal stannates (sodium stannate), alkali metal pyrophosphates (tetrasodium pyrophosphate, disodium pyrophosphate), alkali metal phosphates (sodium phosphate), and phosphoric acid as well as their salts.

The dye preparation and the optional oxidizing agent preparation comprise additional auxiliaries and additives. Thus, it has proven to be inventively preferred when the dye preparation and/or the oxidizing agent preparation comprises at least one thickener. In principle there are no limitations in regard to this thickener. Both organic as well as purely inorganic thickeners can be used.

According to a first preferred embodiment, the thickener is an anionic, synthetic polymer. Carboxylate and sulfonate groups are preferred anionic groups.

Preferred anionic homopolymers are uncrosslinked and crosslinked polyacrylic acids. In this regard, preferred crosslinking agents can be allyl ethers of pentaerythritol, of sucrose and of propylene. Such compounds are commercially available for example, under the trade name Carbopol®. The homopolymer of 2-acrylamido-2-methylpropane sulfonic acid, which is commercially available, for example under the trade name Rheothik® 11-80, is likewise preferred.

Within this first embodiment, it can also be preferred to use copolymers of at least one anionic monomer and at least one non-ionic monomer. Regarding the anionic monomers, reference is made to the abovementioned substances. Preferred non-ionic monomers are acrylamide, methacrylamide, acrylic acid esters, methacrylic acid esters, itaconic acid mono and diesters, vinyl pyrrolidinone, vinyl ethers and vinyl esters.

The anionic acrylic acid and/or methacrylic acid polymers or copolymers are preferably comprised in the inventive agents in an amount of about 0.1 to about 10 wt %, particularly preferably about 1 to about 5 wt %, each relative to the weight of the agent.

Preferred anionic copolymers are for example copolymers of acrylic acid, methacrylic acid or their $C_1$-$C_6$ alkyl esters, as are commercialised under the INCI name Acrylates Copolymers. A preferred commercial product for this is for example Aculyn® 33 from the Rohm & Haas company. However, copolymers of acrylic acid, methacrylic acid or their $C_1$-$C_6$ alkyl esters and of the esters of an ethylenically unsaturated acid and an alkoxylated fatty alcohol are also preferred. Suitable ethylenically unsaturated acids are particularly acrylic acid, methacrylic acid and itaconic acid; suitable alkoxylated fatty alcohols are in particular Steareth-20 or Ceteth-20. These types of copolymer are commercialized by the Rohm & Haas company under the trade name Aculyn® 22 and by the National Starch company under the trade names Structure® 2001 and Structure® 3001.

Preferred anionic copolymers are also acrylic acid-acrylamide copolymers and particularly polyacrylamide copolymers with monomers that contain sulfonic acid groups. A particularly preferred anionic copolymer consists of 70 to 55 mole % acrylamide and 30 to 45 mole % 2-acrylamido-2- methylpropane sulfonic acid, wherein the sulfonic acid group may be fully or partially present as the sodium, potassium, ammonium, mono or triethanolammonium salt. This copolymer can also be crosslinked, wherein the preferred crosslinking agents include polyolefinically unsaturated compounds such as tetraallyloxyethane, allyl sucrose, allyl pentaerythritol and methylene bisacrylamide. Such a polymer is comprised in the commercial product Sepigel®305 and Simulgel® from the SEPPIC company. The use of this compound, which comprises a mixture of hydrocarbons ($C_{13}$-$C_{14}$ isoparaffins or isohexadecane) and a non-ionic emulsifier (Laureth-7 or polysorbate-80) besides the polymer components, has proved to be particularly advantageous in the context of the inventive teaching.

Polymers of maleic anhydride and methyl vinyl ether, in particular those with crosslinks, are also preferred thickeners. A maleic acid-methyl vinyl ether copolymer crosslinked with 1,9-decadiene is commercially available under the trade name Stabileze® QM.

The inventive agent can preferably additionally comprise at least one anionic polymer or copolymer of acrylic acid and/or methacrylic acid. Preferred polymers of this type are:
- polymers of e.g. at least 10 wt % of lower alkyl esters of acrylic acid, about 25 to about 70 wt % of methacrylic acid and optionally up to about 40 wt % of a further comonomer,
- mixed polymers of about 50 to about 75 wt % ethyl acrylate, about 25 to about 35 wt % acrylic acid and 0 to about 25 wt % of other comonomers. Suitable dispersions of this type are commercially available, e.g. under the trade name Latekoll® D (BASF).
- copolymers of about 50 to about 60 wt % ethyl acrylate, about 30 to about 40 wt % methacrylic acid and about 5 to about 15 wt % acrylic acid, crosslinked with ethylene glycol dimethacrylate.

According to another embodiment, the thickener is a cationic, synthetic polymer. In particular, those polymers, in which the quaternary ammonium groups are bonded through a $C_1$-$C_4$ hydrocarbon group to a polymer backbone formed from acrylic acid, methacrylic acid or their derivatives, have proved to be particularly suitable.

Homopolymers of the general Formula (HP-1),

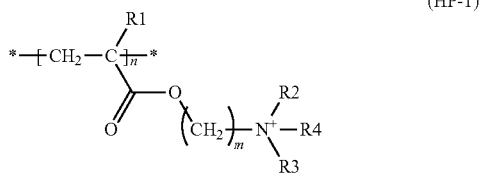

(HP-1)

in which R1=—H or —$CH_3$, R2, R3 and R4 independently of each other are selected from $C_1$-$C_4$ alkyl, -alkenyl or -hydroxyalkyl groups, m=1, 2, 3, or 4, n=a natural number and X⁻ is a physiologically acceptable organic or inorganic anion, as well as copolymers, essentially consisting of the monomer units listed in formula (HP-1) as well as non-ionic monomer units, are particularly preferred cationic polymeric gel formers. Regarding these polymers, those that are preferred in accordance with the invention meet at least one of the following conditions:
- R1 stands for a methyl group
- R2, R3 and R4 stand for methyl groups
- m has the value 2, Exemplary physiologically acceptable counter ions X⁻ include halide ions, sulfate ions, phosphate ions, methosulfate ions as well as organic ions such as lactate, citrate, tartrate and acetate ions. Halide ions are preferred, particularly chloride.

A particularly suitable homopolymer is the optionally crosslinked poly(methacryloxyethyltrimethylammonium chloride) with the INCI name Polyquaternium-37.

Copolymers with monomer units according to formula (HP-1) preferably comprise acrylamide, methacrylamide, $C_1$-$C_4$ alkyl esters of acrylic acid and $C_1$-$C_4$ alkyl esters of methacrylic acid as the non-ionic monomer units. Acrylamide is particularly preferred among these non-ionic monomers. These copolymers can also be crosslinked, as in the case of the above described homopolymers. An inventively preferred copolymer is the crosslinked acrylamide-methacryloxyethyltrimethylammonium chloride copolymer. Such copolymers, in which the monomers are present in a weight ratio of about 20:80, are commercially available as a ca. 50% conc. non-aqueous polymer dispersion named Salcare® SC 92.

In another preferred embodiment, naturally occurring thickeners are employed. Preferred thickeners of this embodiment are for example non-ionic guar gums. Both modified as well as unmodified guar gums can be inventively employed. Non-modified guar gums are sold for example under the trade name Jaguar® C (Rhone Poulenc). Inventively preferred modified guar gums comprise $C_1$-$C_6$ hydroxyalkyl groups. Hydroxymethyl, hydroxyethyl, hydroxypropyl and hydroxybutyl groups are preferred. These kinds of guar gums are known in the prior art and can be produced for example by reacting the guar gum with alkylene oxides. The degree of hydroxyalkylation, corresponding to the number of alkylene oxide molecules used in proportion to the number of free hydroxy groups of the guar gum, is preferably between 0.4 and 1.2. These kinds of modified guar gum are commercially available from Rhone Poulenc under the trade names Jaguar® HP8, Jaguar® HP60, Jaguar® HP 120, Jaguar® DC 293 and Jaguar® HP 105.

Other suitable natural thickeners are likewise known from the prior art.

According to this embodiment, biosaccharide gums of microbial origin are further preferred, such as the scleroglucan gums or Xanthane gums, gums from vegetal exudates, such as for example gum arabicum, ghatti-gum, karaya gum, traganthe gum, carrageen gum, agar-agar, locust bean flour, pectins, alginates, starch fractions and derivatives such as amylose, amylopectin and dextrins, cellulose derivatives, such as for example methyl cellulose, carboxyalkyl celluloses and hydroxyalkyl celluloses.

Preferred hydroxyalkyl celluloses are especially those marketed under the names Cellosize® from Amerchol and Natrosol® from Hercules. Suitable carboxyalkyl celluloses are especially the carboxymethyl celluloses, as are marketed under the names Blanose® from Aqualon, Aquasorb® and Ambergum® from Hercules and Cellgon® from Montello.

Starch and its derivatives are also preferred. Natural starches, obtained from plants, and/or chemically or physically modified starches are inventively employable. Modifications can be achieved for example by introducing different functional groups at one or more of the hydroxy groups of the starch. These are usually esters, ethers or amides of the starch with optionally substituted $C_1$-$C_{40}$ moieties. A maize starch, etherified with a 2-hydroxypropyl group, as is marketed by National Starch under the trade name Amaze®, is particularly advantageous.

However, non-ionic, fully synthetic polymers, such as for example polyvinyl alcohol or polyvinyl pyrrolidinone, can also be employed as the thickeners according to the invention (for example Luviskol®; BASF). In addition to their excellent thickening properties, such non-ionic polymers also confer to the resulting preparations a significant improvement in the sensorial feel.

In the context of the invention, layered silicates (polymers, crystalline sodium disilicates) have proven to be particularly suitable as inorganic thickeners. Especially clays, especially magnesium aluminum silicates, such as for example Bentonite, particularly Smectites, such as Montmorillonite or Hectorite, which can also have been suitably modified, and synthetic layered silicates, such as the layered magnesium silicate, marketed by Süd Chemie under the trade name Optigel®, are preferred.

In order to further enhance the power of the oxidizing agent preparation, an optionally hydrated $SiO_2$ compound can be additionally added to the inventive preparation. According to the invention it may be preferred to use the optionally hydrated $SiO_2$ compounds in amounts of about 0.05% by weight to about 15% by weight, particularly preferably in amounts of about 0.15% by weight to about 10% by weight and quite particularly preferably in amounts of about 0.2% by weight to about 5% by weight, in each case based on the anhydrous agent according to the invention. In this regard, the quantities each reflect the content of the $SiO_2$ compounds (without their water content) in the agents. With regard to the optionally hydrated $SiO_2$ compounds, the present invention is not in principle subject to any limitations. Preference is given to silicic acids, their oligomers and polymers, and their salts. Preferred salts are the alkali metal salts, in particular the potassium and sodium salts. The sodium salts are quite particularly preferred. The optionally hydrated $SiO_2$ compounds can be present in various forms. According to the invention, the $SiO_2$ compounds are preferably used in the form of silica gels or particularly preferably as a water-glass. Some of these $SiO_2$ compounds may be in the form of an aqueous solution. According to the invention, quite particular preference is given to water-glasses that are formed from a silicate of the formula $(SiO_2)_n(Na_2O)_m(K_2O)_p$, where n is a positive rational number and m and p, independently of one another, are a positive rational number or are 0, with the provisos that at least one of the parameters m or p is different from 0 and the ratio between n and the sum of m and p is between about 1:4 and about 4:1. Metasilicates are preferred in which the ratio between n and the sum of m and p is about 1:2 or lower. Besides the components described by the empirical formula, the water-glasses can also comprise, in small amounts, further additives, such as, for example, phosphates or magnesium salts.

The preparation (A) and/or optionally the oxidizing agent preparation (B) are preferably packaged as free-flowing preparations.

An emulsifier or a surfactant is preferably also added to the free-flowing preparations (A) and/or (B), wherein surface active substances are designated as surfactants or as emulsifiers depending on their field of application, and are selected from anionic, cationic, zwitterionic, amphoteric and non-ionic surfactants and emulsifiers. These substances are described in detail below.

Suitable anionic surfactants for the inventive preparations are all anionic surface-active materials that are suitable for use on the human body. Preferred anionic surfactants are alkyl sulfates, alkyl ether sulfates and ether carboxylic acids containing 10 to 18 carbon atoms in the alkyl group and up to 12 glycol ether groups in the molecule.

Zwitterionic surfactants are designated as those surface-active compounds that carry at least one quaternary ammonium group and at least one carboxylate, sulfonate or sulfate group in the molecule. Particularly suitable zwitterionic surfactants are the so-called betaines such as the N-alkyl-N,N-dimethylammonium glycinates, for example the cocoalkyl dimethylammonium glycinate, N-acylaminopropyl-N,N-dimethylammonium glycinates, for example the cocoacylaminopropyldimethylammonium glycinate, and 2-alkyl-3-carboxymethyl-3-hydroxyethyl imidazolines with 8 to 18 carbon atoms in each of the alkyl or acyl groups, as well as cocoacylaminoethyl hydroxyethyl carboxymethyl glycinate. A preferred zwitterionic surfactant is the fatty acid amide derivative, known under the INCI name Cocamidopropyl Betaine.

Ampholytic surfactants are understood to include such surface-active compounds that apart from a $C_8$-$C_{24}$ alkyl or acyl group, comprise at least one free amino group and at least one —COOH or —$SO_3H$ group in the molecule, and are able to form internal salts. Exemplary suitable amphoteric surfactants are N-alkylglycine, N-alkylpropionic acids, N-alkylamino butyric acids, N-alkylimino dipropionic acids, N-hydroxyethyl-N-alkylamido propylglycine, N-alkyltaurine, N-alkylsarcosine, 2-alkylamino propionic acids and alkylamino acetic acids each with about 8 to 24 carbon atoms in the alkyl group. Particularly preferred amphoteric surfactants are the cocoalkylamino propionate, the cocoacylaminoethylamino propionate and the $C_{12}$-$C_{18}$ acylsarcosine.

Furthermore, it has proven advantageous when the dye and lightening agents according to the invention comprise additional non-ionic surface active substances. $C_8$-$C_{22}$ alkyl mono- and oligo-glycosides and their ethoxylated analogs are particularly suitable as the non-ionic surfactants. In particular, the non-ethoxylated compounds have proven to be particularly suitable. Alkylene oxide addition products on saturated, linear fatty alcohols and fatty acids, each with 2 to 30 moles ethylene oxide per mole fatty alcohol or fatty acid, have proved to be additional preferred non-ionic surfactants.

The anionic, non-ionic, zwitterionic or amphoteric surfactants are employed in quantities of about 0.1 to about 45 wt %, preferably about 1 to about 30 wt % and quite particularly preferably from about 1 to about 15 wt %, based on the total amount of the ready-to-use agent.

According to the invention, cationic surfactants of the type quaternary ammonium compounds, the esterquats and the amido amines are likewise preferred. Preferred quaternary ammonium compounds are ammonium halides, particularly chlorides and bromides, such as alkyltrimethylammonium chlorides, dialkyldimethylammonium chlorides and trialkylmethylammonium chlorides, e.g. cetyltrimethylammonium chloride, stearyltrimethylammonium chloride, distearyldimethylammonium chloride, lauryldimethylammonium chloride, lauryldimethylbenzylammonium chloride and tricetylmethylammonium chloride, as well as the imidazolium compounds known under the INCI designations Quaternium-27 and Quaternium-83. The long alkyl chains of the above-mentioned surfactants have preferably 10 to 18 carbon atoms. The quaternized protein hydrolyzates illustrate further inventively usable cationic surfactants. The alkylamido amines are normally manufactured by the amidation of natural or synthetic fatty acids and fatty acid fractions with dialkylamino amines and are characterized, in addition to a good conditioning effect, specifically by their good bio-degradability. According to the invention, a particularly suitable compound from this substance group is represented by stearamidopropyldimethylamine, commercially available under the designation Tegamid® S 18. Esterquats are known compounds, which both comprise at least one ester function and also at least one quaternary ammonium group as structural elements. The products Armocare® VGH-70, an N,N-bis(2-palmitoyloxyethyl)dimethylammonium chloride, as well as Dehyquart® F-75, Dehyquart® C-4046, Dehyquart® L80 and Dehyquart® AU 35 are examples of esterquats.

The agents used according to the invention preferably comprise the cationic surfactants in quantities of about 0.05 to about 10 wt %, based on the total agent. Quantities of about 0.1 to about 5 wt % are particularly preferred.

In a preferred embodiment, non-ionic, zwitterionic and/or amphoteric surfactants as well as mixtures thereof can be preferred.

Furthermore, the inventive agents can comprise additional active substances, auxiliaries and additives, such as for example non-ionic polymers, silicones, cationic polymers, zwitterionic and amphoteric polymers, anionic polymers, additional thickeners, structurants, hair-conditioning compounds, solvents and solubilizers such as ethanol, isopropanol, ethylene glycol, propylene glycol, glycerin and diethylene glycol, fiber structure improvers, colorants for coloring the agent, anti-dandruff active substances, amino acids and oligopeptides, especially arginine and/or serine, protein hydrolyzates as well as in the form of their fatty acid condensation products or optionally anionically or cationically modified derivatives, vegetal oils, light stabilizers, active substances such as panthenol, pantothenic acid, pantolactone, allantoin, pyrrolidinone carboxylic acids and their salts as well as bisabolol, ceramide, vitamins, provitamins and vitamin precursors, plant extracts, cholesterol, texturizers, fatty alcohols, fats and waxes, fatty acid alkanolamides, swelling and penetration substances, opacifiers such as latex, styrene/PVP copolymers and styrene/acrylamide copolymers, pearlizers such as ethylene glycol mono and distearate as well as PEG-3-distearate, pigments, blowing agents such as propane-butane mixtures, $N_2O$, dimethyl ether, $CO_2$ and air; antioxidants.

The person skilled in the art will select these additional materials as a function of the desired properties of the agent. With regard to further optional ingredients and their amounts used, reference is expressly made to the relevant handbooks known to the person skilled in the art, for example the monograph by K. Schrader, Grundlagen and Rezepturen der Kosmetika, 2nd edition, Hüthig Buch Verlag, Heidelberg, 1989.

The additional active substances and auxiliaries are preferably incorporated in the agents according to the invention in amounts of about 0.0001 to about 10 wt %, particularly about 0.0005 to about 5 wt %, based on the total weight of the application mixture.

Employing only hydrogen peroxide or its addition products on organic or inorganic compounds is often insufficient for strongly lightening very dark hair. Consequently, the agents according to the invention can additionally comprise still further blonding and/or bleaching agents.

If a strong lightening is desired in addition to dyeing the keratinic fibers, then it is inventively preferred to additionally mix a blonde-dyeing preparation (C) that comprises at least one bleach booster with the mixture of the oxidizing agent preparation (B) and the preparation (A), comprising at least one oxidation dye precursor according to Formula (I).

In this regard, it can be irrelevant whether a mixture of (A) and (B) is initially produced and then the blonde-dyeing preparation (C) is blended in, or whether a different sequence of blending of the individual components is utilized. It is preferred to blend the individual preparations in the shortest possible period of time and to apply the ready-to-use agent preferably promptly onto the keratinic fibers.

Consequently, another embodiment of the present application is an agent for bleaching and dyeing keratinic fibers, characterized in that it is produced prior to the application by blending at least one oxidizing agent preparation (B) that comprises at least one oxidizing agent, selected from hydrogen peroxide and its addition products on solid carriers, with at least one blond-dyeing preparation (C) that comprises at least one bleach booster, and at least one preparation (A), comprising in a cosmetic carrier at least one oxidation dye precursor according to Formula (I).

In another embodiment, it is preferred when the colorant according to the invention additionally comprises at least one inorganic peroxo compound as the blonding preparation (C). The inorganic peroxo compound is preferably selected from ammonium persulfate, alkali metal persulfates, ammonium peroxomonosulfate, alkali metal hydrogen peroxomonosulfates, alkali metal peroxodiphosphates and alkaline earth metal peroxides. The inorganic peroxo compounds are preferably comprised in an amount of about 0.1 to about 25 wt %, particularly in an amount of about 0.5 to about 15 wt %, based on the total weight of the ready for use agent.

The persulfate salts or peroxodisulfate salts are generally added in the form of an optionally de-dusted powder or in the form of a compressed molded body.

Although in principle there is no limitation in regard to the formulation of the blonding preparation (C), it has proved to be inventively preferred when the preparation (C) is an anhydrous formulation.

In the context of the present invention, anhydrous means a water content, based on the preparation (C), of less than about 5 wt %, especially less than about 2 wt %. Blonding preparations that comprise less than about 0.1 wt % water can be inventively quite particularly preferred. The preparation (C) is preferably formulated as a powder or an anhydrous paste.

In another preferred embodiment, the agent in the preparation (C) can comprise at least one cationic pyridinium derivative as the bleach booster. Inventive agents are particularly preferred which comprise a compound from 2-acetyl-1-methylpyridinium p-toluene sulfonate and/or 4-acetyl-1-methylpyridinium p-toluene sulfonate and/or N-methyl-3,4-dihydroisoquinolinium p-toluene sulfonate as the cationic pyridinium derivative.

An inventively preferred embodiment of the present invention consists in that the ready-to-use agent exhibits a pH between about 7 and about 11, particularly between about 8 and about 10.5, particularly preferably between about 8.5 and about 10.0.

The pH is usually adjusted with pH adjustors. The person skilled in cosmetics commonly uses established acidifiers and alkalizers to adjust the pH. The alkalizers that can be used for adjusting the pH are typically selected from inorganic salts, especially from the alkali metals and alkaline earth metals, organic alkalizers, especially amines, basic amino acids and alkanolamines, and ammonia. Inventively preferred acidifiers are food acids, such as for example citric acid, acetic acid, malic acid or tartaric acid, as well as diluted mineral acids.

In the context of the present invention, the pH values refer to those measured at a temperature of 22° C.

Inventively useable organic alkalizers are preferably selected from alkanolamines from primary, secondary or tertiary amines containing a $C_2$-$C_6$ alkyl parent substance that carries at least one hydroxyl group. Particularly preferred alkanolamines are selected from the group 2-aminoethan-1-ol, 2-amino-2-methylpropan-1-ol 2-amino-2-methyl-propane-1,3-diol and triethanolamine Inorganic alkalizers are preferably selected from sodium hydroxide, potassium hydroxide, calcium hydroxide, barium hydroxide, sodium phosphate, potassium phosphate, sodium silicate, potassium silicate, sodium carbonate and potassium carbonate. Sodium hydroxide and/or potassium hydroxide are quite particularly preferred. The basic amino acids are preferably selected from L-arginine, D-arginine, D/L-arginine, L-lysine, D-lysine, D/L-lysine, particularly preferably L-arginine, D-arginine and D/L-arginine. Finally, ammonia is another preferred alkalizer.

The alkalizers are preferably comprised in amounts of about 0.05 to about 10 wt %, particularly about 0.5 to about 5 wt %, each based on the total weight of the ready-to-use agent.

As already mentioned, the agents according to the invention can also be produced from two or more separately packaged preparations immediately prior to use. This lends itself in particular to the separation of incompatible ingredients in order to avoid premature reaction. A separation into multi-component systems is particularly appropriate in cases where incompatibilities of the ingredients are to be expected or to be feared. In systems of this type, the ready-to-use agent is produced by the user by blending the components immediately prior to use. A dyeing and/or lightening agent, in which the oxidation dye precursors are initially separated from the oxidizing agent preparation, is preferred in this regard.

A further preferred presentation form of the agent according to the invention is a kit-of-parts that in separately packaged containers comprises in a container A at least one preparation (A), comprising in a cosmetic carrier at least one oxidation dye precursor according to the Formula (I), and
  in a container B at least one oxidizing agent preparation (B), comprising in a cosmetic carrier at least one oxidizing agent.

If a particularly strong lightening effect is desired, then a further preferred presentation form of the agent according to the invention is a kit-of-parts that in separately packaged containers comprises in a container A at least one preparation (A), comprising in a cosmetic carrier at least one oxidation dye precursor according to the Formula (I),
  in a container B at least one oxidizing agent preparation (B), comprising at least one oxidizing agent, and
  in a container C at least one blonding preparation (C), comprising at least one bleach booster.

The multi-component kit-of-parts preferably additionally comprises an instruction manual. Moreover, it can be preferred that an application aid, such as for example a comb or a brush, and/or a personal protection kit, such as for example disposable gloves, is supplied with the kit.

With reference to further preferred embodiments of the multi-component kit-of-parts, the statement made concerning the agents according to the invention applies mutatis mutandis.

The actual hair dye is advantageously produced immediately prior to the application by mixing the preparations (A) with (B) as well as optionally (C). The application temperatures can be in a range between about 15 and about 40° C. After a contact time of about 5 to about 45 minutes, the hair dye is removed from the hair by rinsing. There is no need to wash the hair with a shampoo afterwards if a strong surfactant-containing carrier, e.g. a color enhancing shampoo, was used.

Accordingly, another subject matter of the present invention is a method for dyeing and optionally lightening human hair, in which an agent according to the invention according to the above specifications is deposited on the hair, the agent being left on the hair for a contact time of about 5 to about 45 minutes, preferably about 8 to about 35 minutes, and is subsequently rinsed out of the hair and/or washed out with a shampoo.

During the contact time of the agent with the fibers, it can be advantageous to support the dyeing process by supplying heat. The supply of heat can be from a heat source, such as e.g. warm air from a stream of warm air, as also, especially for a hair coloration on living subjects, from the body temperature of the subject. For the latter alternative, the areas being dyed are normally covered with a cap. In particular, the temperature during the contact time is between about 10° C. and about 45° C., particularly between about 20° C. and about 40° C. The inventive dyes furnish intensive colorations already at physiologically compatible temperatures of below about 45° C. In consequence, they are particularly suitable for dyeing human hair.

A further subject matter of the present invention is the use of an agent according to the invention in oxidative dyes for human hair so as to improve the gray coverage, the levelling, the color intensity, the durability and/or the vividness of the dyeing results.

With reference to further preferred embodiments of the method according to the invention, the statement made concerning the agents according to the invention applies mutatis mutandis.

Finally, another subject matter of the present invention relates to compounds according to Formula (I) of the first subject matter of the invention. With reference to further preferred embodiments of these compounds, the statement made concerning the agents according to the invention applies mutatis mutandis.

EXAMPLES

Synthetic Examples

Synthetic Example 1

N,N-Dimethyl-3-[(4-aminophenyl)amino]-N-{3-[(4-aminophenyl)amino]propyl)-1-propanaminium p-toluene sulfonate, tetrahydrochloride (E1)

1.1 Synthesis of N1-methyl-N3-(4-nitrophenyl)-N1-{3-[(4-nitrophenyl)amino]propyl}-1,3-propanediamine 4-Chloronitrobenzene, 50.0 g (0.32 mol), in 100 ml dimethylsulfoxide were heated to 80° C. (clear solution). Sodium carbonate, 15.6 g (0.16 mol), was then added. N1-(3-Aminopropyl)-N1-methyl-1,3-propanediamine, 23.2 g (0.16 mol), was then added dropwise at this temperature. Following the dropwise addition the reaction mixture was then stirred for 12 h at 120° C. After cooling, water (1 l) was added and the aqueous phase was extracted 3 times with 200 ml ethyl acetate. The organic phase was then dried with sodium sulfate and concentrated under vacuum in a rotovap. The product remained as a residue in the form of a highly viscous oil. Yield: 48.1 g (78.2%); $^1$H-NMR (400 MHz, DMSO-$d_6$): δ [ppm]=1.71 (m, 4H); 2.17 (s, 3H); 2.40 (t, 4H); 3.18 (m, 4H); 6.61 (d, 4H); 7.27 (br., 2×NH); 7.98 (d, 4H).

1.2. Synthesis of N,N-dimethyl-3-[(4-nitrophenyl)amino]-N-{3-[(4-nitrophenyl)amino]propyl}-1-propanaminium p-toluene sulfonate N1-Methyl-N3-(4-nitrophenyl)-N1-{3-[(4-nitrophenyl)amino]propyl}-1,3-propanediamine (40.0 g, 0.10 mol) from step 1.1. was heated under reflux with methyl p-toluene sulfonate (20.5 g, 0.11 mol) in 500 ml toluene. The educt to be quaternized was not initially soluble in toluene but slowly passed into solution on heating. In the course of the reaction the product separated out in the form of an oily substance that was separated by decanting the supernatant solution. The oil was again stirred with 300 ml toluene and then dried under a vacuum. Yield: 14.6 g (24.7%); $^1$H-NMR (400 MHz, DMSO-$d_6$): δ [ppm]=2.03 (m, 4H); 2.30 (s, 3H); 3.08 (s, 6H); 3.22 (m, 4H); 3.43 (m, 4H); 6.67 (d, 4H); 7.16 (d, 2H); 7.59 (d, 2H); 8.01 (d, 4H).

1.3. Synthesis of N,N-dimethyl-3-[(4-aminophenyl)amino]-N-{3-[(4-aminophenyl)amino]propyl}-1-propanaminium p-toluene sulfonate, tetrahydrochloride (E1)

N,N-dimethyl-3-[(4-nitrophenyl)amino]-N-{3-[(4-nitrophenyl)amino]propyl}-1-propanaminium p-toluene sulfonate (54.0 g, 0.09 mol) from step 1.2. was dissolved in 900 ml ethanol and 100 ml distilled water. Palladium on charcoal (5%, 0.5 g) was added as the catalyst, the mixture was then hydrogenated in the autoclave at room temperature and under a hydrogen pressure of 10 bar. After the reduction was completed the amino compound was filtered off from the catalyst and converted to the hydrochloride salt by the addition of 150 ml half-concentrated hydrochloric acid to the filtrate. The filtrate was then concentrated down to afford the product in the form of a reddish, crystalline solid. Yield: 26.9 g (50.9%); $^1$H-NMR (400 MHz, DMSO-$d_6$): δ [ppm]=2.14 (m, 4H); 2.30 (s, 3H); 3.09 (s, 6H); 3.24 (m, 4H); 3.52 (m, 4H); 7.12 (d, 2H); 7.19 (d, 4H); 7.34 (d, 4H); 7.51 (d, 2H).

Synthetic Example 2

N-Ethyl-N-methyl-3-[(4-aminophenyl)amino]-N-{3-[(4-aminophenyl)amino]propyl}-1-propanaminium p-toluene sulfonate, tetrahydrochloride (E 2)

2.1 Synthesis of N1-methyl-N3-(4-nitrophenyl)-N1-{3-[(4-nitrophenyl)amino]propyl}-1,3-propanediamine cf. synthesis example 1, step 1.1.

2.2. Synthesis of N-ethyl-N-methyl-3-[(4-nitrophenyl)amino]-N-{3-[(4-nitrophenyl)amino]-propyl}-1-propanaminium p-toluene sulfonate N1-methyl-N3-(4-nitrophenyl)-N1-{3-[(4-nitrophenyl)amino]propyl}-1,3-propanediamine (40.0 g, 0.10 mol) from step 2.1. was heated under reflux with ethyl p-toluene sulfonate (20.5 g, 0.11 mol) in 500 ml toluene for 6 hours. As the reaction progressed the product separated out in the form of an oily substance. This oil was decanted off from the supernatant liquid and stirred with 500 ml toluene. The oil was removed mechanically from the flask, dried and crushed. Yield: 43.0 g (70.8%); $^1$H-NMR (400 MHz, DMSO-$d_6$): δ [ppm]=1.19 (t, 3H); 1.96 (m, 4H); 2.29 (s, 3H); 2.98 (s, 3H); 3.27 (m, 4H); 3.33 (m, 6H); 6.68 (d, 4H); 7.17 (d, 2H); 7.39 (br., 2×NH); 7.56 (d, 2H); 8.01 (d, 4H).

2.2. Synthesis of N-ethyl-N-methyl-3-[(4-nitrophenyl)amino]-N-{3-[(4-nitrophenyl)amino]-propyl}-1-propanaminium p-toluene sulfonate N-Ethyl-N-methyl-3-[(4-nitrophenyl)amino]-N-{3-[(4-nitrophenyl)amino]propyl}-1-propanaminium p-toluene sulfonate (37.8 g, 64 mmol) from step 2.2. was dissolved in 900 ml ethanol and 100 ml distilled water. Palladium on charcoal (5%, 0.5 g) was added as the catalyst, the mixture was then hydrogenated in the autoclave at room temperature and under a hydrogen pressure of 15 bar. After the reduction was completed the amino compound was filtered off from the catalyst and converted to the hydrochloride salt by the addition of 150 ml half-concentrated hydrochloric acid to the filtrate. The filtrate was then concentrated down to afford the product in the form of a brown, crystalline solid. Yield: 27.8 g (75.1%); $^1$H-NMR (400 MHz, DMSO-$d_6$): δ [ppm]=1.31 (t, 3H); 2.28 (m, 4H); 2.36 (s, 3H); 3.09 (s, 3H); 3.44 (m, 6H); 3.54 (m, 4H); 7.29 (d, 2H); 7.59 (m, 8H); 7.62 (d, 2H).

Synthetic Example 3

N-Methyl-N-propyl-3-[(4-aminophenyl)amino]-N-{3-[(4-aminophenyl)-amino]propyl}-1-propanaminium p-toluene sulfonate, tetrahydrochloride (E3)

3.1. Synthesis of N1-Methyl-N3-(4-nitrophenyl)-N1-{3-[(4-nitrophenyl)amino]propyl}-1,3-propanediamine cf. synthesis example 1, step 1.1.

3.2. Synthesis of N-allyl-N-methyl-3-[(4-nitrophenyl)amino]-N-{3-[(4-nitrophenyl)amino]propyl}-1-propanaminium p-toluene sulfonate N1-Methyl-N3-(4-nitrophenyl)-N1-{3-[(4-nitrophenyl)amino]propyl}-1,3-propanediamine (40.0 g, 0.10 mol) from step 3.1. was heated under reflux with allyl p-toluene sulfonate (29.4 g, 0.11 mol) in 500 ml toluene for 6 hours. As the reaction progressed the product separated out in the form of an oily substance. This oil was decanted off from the supernatant liquid and stirred with 300 ml toluene. The product was then dried and crushed. Yield: 43.9 g (70.0%); $^1$H-NMR (400 MHz, DMSO-$d_6$): δ [ppm]=1.98 (m, 4H); 2.29 (s, 3H); 3.00 (s, 3H); 3.22 (m, 4H); 3.38 (m, 4H); 3.99 (d, 2H); 5.15 (dd, 1H); 5.55 (dd, 1H); 6.04 (m, 1H); 6.67 (d, 4H); 7.12 (d, 2H); 7.53 (d, 2H); 7.98 (d, 4H).

3.3. Synthesis of N-methyl-N-propyl-3-[(4-aminophenyl)amino]-N-{3-[(4-aminophenyl)amino]-propyl}-1-propanaminium p-toluene sulfonate, tetrahydrochloride (E3)

N-Allyl-N-methyl-3-[(4-nitrophenyl)amino]-N-{3-[(4-nitrophenyl)amino]propyl}-1-propanaminium p-toluene sulfonate (37.8 g, 64.3 mmol) from step 3.2. was dissolved in 900 ml ethanol and 100 ml distilled water. Palladium on charcoal (5%, 0.5 g) was added as the catalyst, the mixture was then hydrogenated in the autoclave at room temperature and under a hydrogen pressure of 15 bar. After the reduction was completed the amino compound was filtered off from the catalyst and converted to the tetrahydrochloride salt by the addition of 150 ml half-concentrated hydrochloric acid to the filtrate. The filtrate was then concentrated down to afford the product in the form of a light brown, crystalline solid. Yield: 15.4 g (39.7%).

Synthetic Example 4

N1,N4-Bis-{3-[(4-aminophenyl)amino]propyl}-N1-methylpiperazinium p-toluene sulfonate, hydrochloride salt (E 4)

4.1. Synthesis of N1,N4-Bis-(4-nitrophenyl)-1,4-piperazinedipropanamine

4-Fluoronitrobenzene (28.2 g, 0.20 mol) 1,4-bis(3-aminopropyl)piperazine (21.0 g, 0.10 mol) and triethylamine (61.8 g, 0.61 mol) were stirred together in 200 ml dimethylsulfoxide for 10 hours at 80° C. 40 ml of water were then added and stirring was continued for a further 3 hours at 80° C. (formation of a precipitate). After cooling, the mixture was poured onto 1 l water. The precipitated solid was filtered off, washed with water and dried under vacuum. Yield: 40.2 g (90.7%); $^1$H-NMR (400 MHz, DMSO-$d_6$): δ [ppm]=1.69 (m, 4H); 2.38 (m, 12H); 3.18 (m, 4H); 6.63 (d, 4H); 7.32 (br., 2×NH); 7.99 (d, 4H).

4.2. Synthesis of N1,N4-Bis-{3-[(4-nitrophenyl)amino]propyl}-N1-methylpiperazinium p-toluene sulfonate N1,N4-Bis-(4-nitrophenyl)-1,4-piperazinedipropanamine (35.0 g, 0.079 mol) from step 6.1. was heated under reflux with methyl p-toluene sulfonate (16.2 g, 0.087 mol) in 400 ml toluene for 6 hours. In the course of the reaction the product separated out in the form of an oily substance that was separated by decanting the supernatant solution. On further cooling, the oil solidified in a glassy form, after drying could be pulverized, such that the product was obtained in the form of a yellow solid. Yield: 45.1 g (90.7%).

4.3. Synthesis of N1,N4-Bis-{3-[(4-aminophenyl)amino]propyl}-N1-methylpiperazinium p-toluene sulfonate, hydrochloride salt (E 4)

N1,N4-Bis-{3-[(4-nitrophenyl)amino]propyl}-N1-methylpiperazinium p-toluene sulfonate (38.4 g, 61.1 mmol) from step 4.2. was dissolved in 900 ml ethanol and 100 ml distilled water. Palladium on charcoal (5%, 0.5 g) was added as the catalyst, the mixture was then hydrogenated in the autoclave at room temperature and under a hydrogen pressure of 10 bar. After the reduction was completed the amino compound was filtered off from the catalyst and converted to the hydrochloride salt by the addition of 150 ml half-concentrated hydrochloric acid to the filtrate. The filtrate was concentrated down to afford the brown, waxy product. Yield: 20.8 g (53.2%).

Synthesis Example 5

N,N-Dimethyl-3-[(4-amino-3-methylphenyl)amino]-N-{3-[(4-amino-3-methylphenyl)amino]propyl}-1-propanaminium p-toluene sulfonate, tetrahydrochloride (E 5)

5.1. Synthesis of N1-Methyl-N3-(3-methyl-4-nitrophenyl)-N1-{3-[(3-methyl-4-nitrophenyl)-amino]propyl}-1,3-propanediamine To 5-fluoro-2-nitrotoluene (50.0 g, 0.32 mol) was added sodium carbonate (17.1 g, 0.16 mol) at 60° C. 3,3'-Diamino-N-methyldipropylamine (23.7 g, 0.16 mol) was then carefully added dropwise (exothermic reaction). The resulting mixture was heated at 100° C. for 12 hours. 100 ml toluene were added to the cooled reaction mixture causing the inorganic salts to precipitate, which were filtered off. The organic phase was then concentrated down under vacuum in a rotovap to afford the product as a residue in the form of a yellow orange oil. Yield: 52.5 g (78.4%); $^1$H-NMR (400 MHz, DMSO-$d_6$): δ [ppm]=1.71 (m, 4H); 2.18 (s, 3H); 2.40 (m, 4H); 2.55 (s, 6H); 3.17 (m, 4H); 6.45 (s, 2H); 6.48 (d, 2H); 7.08 (br., 2×NH); 7.92 (d, 2H).

5.2. Synthesis of N,N-Dimethyl-3-[(3-methyl-4-nitrophenyl)amino]-N-{3-[(3-methyl-4-nitrophenyl)amino]propyl}-1-propanaminium p-toluene sulfonate N1-Methyl-N3-(3-methyl-4-nitrophenyl)-N1-{3-[(3-methyl-4-nitrophenyl)-amino]propyl}-1,3-propanediamine (57.0 g, 0.14 mol) from step 5.1. was heated under reflux with methyl p-toluene sulfonate (28.4 g, 0.15 mol) in 500 ml toluene for 6 hours. As the reaction progressed the product separated out in the form of an oily substance. This oil was decanted off from the supernatant liquid, stirred with 300 ml toluene and dried. On further cooling the oil initially solidified to a glassy material and after drying could be crushed to afford the product as a brown powder. Yield: 58.4 g (70.8%); $^1$H-NMR (400 MHz, DMSO-$d_6$): δ [ppm]=1.98 (m, 4H); 2.29 (s, 3H); 2.51 (s, 6H); 3.17 (s, 6H); 3.21 (m, 4H); 3.40 (m, 4H); 6.51 (s, 2H); 6.52 (d, 2H); 7.17 (d, 2H); 7.59 (d, 2H); 7.98 (d, 2H).

5.3. Synthesis of N,N-Dimethyl-3-[(4-amino-3-methylphenyl)amino]-N-{3-[(4-amino-3-methylphenyl)amino]propyl}-1-propanaminium p-toluene sulfonate, tetrachloride (E 5)

N,N-Dimethyl-3-[(3-methyl-4-nitrophenyl)amino]-N-{3-[(3-methyl-4-nitrophenyl)amino]propyl}-1-propanaminium p-toluene sulfonate (58.0 g, 86.7 mmol) from step 5.2. was dissolved in 900 ml ethanol and 100 ml distilled water. Palladium on charcoal (5%, 0.5 g) was added as the catalyst, the mixture was then hydrogenated in the autoclave at room temperature and under a hydrogen pressure of 15 bar. After the reduction was completed the amino compound was filtered off from the catalyst and converted to the hydrochloride salt by the addition of 150 ml half-concentrated hydrochloric acid to the filtrate. The filtrate was then concentrated down to afford the product in the form of a light red, crystalline solid. Yield: 52.0 g (87.8%); $^1$H-NMR (400 MHz, DMSO-$d_6$): δ [ppm]=2.18 (m, 4H); 2.33 (s, 6H); 2.41 (s, 3H); 3.14 (s, 6H); 3.30 (m, 4H); 3.59 (m, 4H); 7.19 (d, 2H); 7.30-7.55 (m, 8H).

Synthesis Example 6

N-Ethyl-N-methyl-3-[(4-amino-3-methylphenyl)amino]-N-{3-[(4-amino-3-methylphenyl)amino]propyl}-1-propanaminium p-toluene sulfonate, tetrahydrochloride (E 6)

6.1. Synthesis of N1-Methyl-N3-(3-methyl-4-nitrophenyl)-N1-{3-[(3-methyl-4-nitrophenyl)-amino]propyl}-1,3-propanediamine cf. synthesis example 5, step 5.1.

6.2. Synthesis of N-Ethyl-N-methyl-3-[(3-methyl-4-nitrophenyl)amino]-N-{3-[(3-methyl-4-nitrophenyl)amino]propyl}-1-propanaminium p-toluene sulfonate N1-Methyl-N3-(3-methyl-4-nitrophenyl)-N1-{3-[(3-methyl-4-nitrophenyl)-amino]propyl}-1,3-propanediamine (52.0 g, 0.13 mol) from step 6.1 was heated under reflux with ethyl p-toluene sulfonate (28.0 g, 0.14 mol) in 500 ml toluene for 6 hours. As the reaction progressed the product separated out in the form of an oily substance. This oil was separated from the supernatant liquid by decanting and dried. On further cooling the oil initially solidified to a glassy material and after drying could be crushed to afford the product as a brown powder. Yield: 60.9 g (79.1%); $^1$H-NMR (400 MHz, DMSO-$d_6$): δ [ppm]=1.21 (t, 3H); 1.97 (m, 4H); 2.29 (s, 3H); 2.99 (s, 3H); 3.23 (m, 4H); 3.33 (m, 4H); 3.43 (q, 2H); 6.50 (dd, 2H); 6.55 (dd, 2H); 7.18 (d, 2H); 7.20 (br. 2×NH); 7.54 (d, 2H); 7.96 (d, 2H).

6.3. Synthesis of N-Ethyl-N-methyl-3-[(4-amino-3-methylphenyl)amino]-N-{3-[(4-amino-3-methylphenyl)amino]propyl}-1-propanaminium p-toluene sulfonate, tetrachloride (E 6)

N-Ethyl-N-methyl-3-[(3-methyl-4-nitrophenyl)amino]-N-{3-[(3-methyl-4-nitrophenyl)amino]propyl}-1-propanaminium p-toluene sulfonate (50.5 g, 82 mmol) from step 6.2. was dissolved in 900 ml ethanol and 100 ml distilled water. Palladium on charcoal (5%, 0.5 g) was added as the catalyst, the mixture was then hydrogenated in the autoclave at room temperature and under a hydrogen pressure of 10 bar. After the reduction was completed the amino compound was filtered off from the catalyst and converted to the tetrahydrochloride salt by the addition of 150 ml half-concentrated hydrochloric acid to the filtrate. The filtrate was then concentrated down to afford the product in the form of a beige, crystalline solid. Yield: 21.6 g (41.9%); $^1$H-NMR (400 MHz, DMSO-$d_6$): δ [ppm]=1.32 (t, 3H); 2.27 (m, 4H); 2.36 (s, 3H); 2.48 (s, 6H); 3.09 (s, 3H); 3.45 (m, 6H); 3.55 (m, 4H); 7.27 (d, 2H); 7.47 (dd, 2H); 7.58 (dd, 2H); 7.59 (d, 2H); 7.63 (d, 2H).

Synthesis Example 7

N-Methyl-N-propyl-3-[(4-amino-3-methylphenyl)amino]-N-{3-[(4-amino-3-methylphenyl)amino]propyl}-1-propanaminium p-toluene sulfonate, tetrahydrochloride (E 7)

7.1. Synthesis of N1-Methyl-N3-(3-methyl-4-nitrophenyl)-N1-{3-[(3-methyl-4-nitrophenyl)amino]propyl}-1,3-propanediamine cf. synthesis example 5, step 5.1.

7.2. Synthesis of N-allyl-N-methyl-3-[(3-methyl-4-nitrophenyl)amino]-N-{3-[(3-methyl-4-nitrophenyl)amino]propyl}-1-propanaminium p-toluene sulfonate N1-Methyl-N3-(3-methyl-4-nitrophenyl)-N1-{3-[(3-methyl-4-nitrophenyl)amino]propyl}-1,3-propanediamine (60.2 g, 0.14 mol) from step 7.1 was heated under reflux with allyl p-toluene sulfonate (34.0 g, 0.16 mol) in 500 ml toluene for 6 hours. As the reaction progressed the product separated out in the form of an oily substance. This oil was separated from the supernatant liquid by decanting and dried. On further cooling the oil initially solidified to a glassy material and after drying could be crushed to afford the product as a brown powder. Yield: 66.0 g (72.5%).

7.3. Synthesis of N-Methyl-N-propyl-3-[(4-amino-3-methylphenyl)amino]-N-{3-[(4-amino-3-methylphenyl)amino]propyl}-1-propanaminium p-toluene sulfonate, tetrachloride (E 7)

N-allyl-N-methyl-3-[(3-methyl-4-nitrophenyl)amino]-N-{3-[(3-methyl-4-nitrophenyl)amino]propyl}-1-propanaminium p-toluene sulfonate (56.0 g, 89.2 mmol) from step 7.2. was dissolved in 900 ml ethanol and 100 ml distilled water. Palladium on charcoal (5%, 0.5 g) was added as the catalyst, the mixture was then hydrogenated in the autoclave at room temperature and under a hydrogen pressure of 15 bar. After the reduction was completed the amino compound was filtered off from the catalyst and converted to the hydrochloride salt by the addition of 150 ml half-concentrated hydrochloric acid to the filtrate. The filtrate was then concentrated down to afford the product in the form of a brown, crystalline solid. Yield: 18.1 g (37.6%).

EXAMPLES

Coloration Examples

Preparation of the Colorant Creams

The following colorant creams were produced:

| | |
|---|---|
| Hydrenol D | 8.5 wt % |
| Lorol tech. | 2.0 wt % |
| Texapon NSO UP | 20.0 wt % |
| Dehyton K | 12.5 wt % |
| Eumulgin B2 | 0.75 wt % |
| Sodium sulfite | 1.0 wt % |
| Ammonium sulfate | 1.0 wt % |
| Developer component E1 | 3 mmol |
| Coupler component | 3 mmol |
| Water | ad 100 wt % |

Employed Raw Materials:

Hydrenol D C12-C18-fatty alcohol, (INCI name: Cetearylalcohol; Cognis)

Lorol techn. C12-/C18-fatty alcohol, (INCI name: Cetearylalcohol; Cognis)

Texapon NSO UP lauryl alcohol diglycol ether sulfate, Na-salt (28% solution) (INCI-name: Sodium Laureth Sulfate; Cognis)

Dehyton K Cocoyl-betaine (INCI name: Cocamidopropyl betaine; Cognis)

Eumulgin B2 C16-/C18 fatty alcohol, ethoxylated (20 EO) (INCI name: Ceteareth-10; Cognis)

Hydrenol D and Lorol, techn. were melted together with Texapon NSO-UP, Dehyton K and Eumulgin B2 at 80° C. The melt was then emulsified with sodium sulfite and ammonium sulfite dissolved in part of the water. The developer according to the invention was dissolved with heating in propylene glycol and another part of the cited amount of water and added with stirring. The coupler was likewise dissolved in a part of the cited amount of water and added with stirring. Water was then added to make up 100% and the formulation was stirred without heating.

The resulting coloration cream was blended in the ratio 2:1 with the following developer dispersion with a hydrogen peroxide content of 3%.

| | |
|---|---|
| Dipicolinic acid | 0.1 wt % |
| Sodium pyrophosphate | 0.03 wt % |
| Turpinal SL | 1.50 wt % |
| Texapon N28 | 2.00 wt % |
| Acrysol 22 | 0.60 wt % |
| Hydrogen peroxide, 50 wt % conc. | 6.00 wt % |
| Sodium hydroxide, 45 wt % conc. | 0.80 wt % |
| Water | ad 100 wt % |

Employed Raw Materials:

Turpinal SL 1-hydroxyethane-1,1-(diphosphonic acid (ca. 58-61% active substance content; INCI-name: Etidronic Acid, Aqua (Water)) (Solutia)

Texapon N28 Lauryl ether sulfate sodium salt (min. 26.5% active substance content; INCI name: Sodium Laureth Sulfate) (Cognis)

Acrysol 22 Acrylic polymer (ca. 29.5-30.5% solids in water; INCI name:

Acrylates/Steareth-20 Methacrylate Copolymer)

Mixing with the developer dispersion and application

In the dyeing method, the 4 times amount of the ready-for-use mixture was applied to each strand of 80.5 gray hair (Kerling). After a contact time of 30 minutes at 32° C., the strands were rinsed off and washed out with a typical hair shampoo. The coloration of the strands was determined visually after drying under the daylight lamp. The coloration results are summarized in the following Table.

E1: N,N-dimethyl-3-[(4-aminophenyl)amino]-N-{3-[(4-aminophenyl)amino]propyl}-1-propanaminium p-toluene sulfonate, tetrahydrochloride

| Example | Coupler component | Obtained nuance | Color intensity |
|---|---|---|---|
| E1-1 | Resorcinol | earthy brown | +++ |
| E1-2 | 3-Amino-2-methylamino-6-methoxypyridine | thunderstorm blue | +++ |
| E1-3 | 5-Amino-2-methylphenol | dark magenta | +++ |
| E1-4 | 3-Amino-2-hydroxypyridine | gray brown | +++ |
| E1-5 | 1,3-Bis(2,4-diaminophenoxy)propane | ink blue | +++ |
| E1-6 | 2,7-Dihydroxynaphthalene | smoky brown | ++ |

E2: N-ethyl-N-methyl-3-[(4-aminophenyl)amino]-N-{3-[(4-aminophenyl)amino]propyl}-1-propan-aminium p-toluene sulfonate, tetrahydrochloride

| Example | Coupler component | Obtained nuance | Color intensity |
|---|---|---|---|
| E2-1 | Resorcinol | browny gray | +++ |
| E2-2 | 3-Amino-2-methylamino-6-methoxypyridine | blue gray | +++ |
| E2-3 | 5-Amino-2-methylphenol | aubergine | +++ |
| E2-4 | 3-Amino-2-hydroxypyridine | dark blue ruby | +++ |
| E2-5 | 1,3-Bis(2,4-diaminophenoxy)propane | blue black | +++ |
| E2-6 | 2,7-Dihydroxynaphthalene | earthy brown | ++ |

E3: N-methyl-N-propyl-3-[(4-aminophenyl)amino]-N-{3-[(4-aminophenyl)amino]propyl}-1-propan-aminium p-toluene sulfonate, tetrahydrochloride

| Example | Coupler | obtained nuance | color intensity |
|---|---|---|---|
| E3-1 | Resorcinol | brown gray | +++ |
| E3-2 | 3-Amino-2-methylamino-6-methoxypyridine | blue gray | +++ |
| E3-3 | 5-Amino-2-methylphenol | dark magenta | +++ |
| E3-4 | 3-Amino-2-hydroxypyridine | gray brown | ++ |
| E3-5 | 1,3-Bis(2,4-diaminophenoxy)propane | black blue | +++ |
| E3-6 | 2,7-Dihydroxynaphthalene | green gray | ++ |

E4: N1,N4-Bis-{3-[(4-aminophenyl)amino]propyl}-N1-methylpiperazinium p-toluene sulfonate, hydrochloride salt

| Example | Coupler component | Obtained nuance | Color intensity |
|---|---|---|---|
| E4-1 | Resorcinol | browny gray | ++ |
| E4-2 | 3-Amino-2-methylamino-6-methoxypyridine | blue gray | +++ |
| E4-3 | 5-Amino-2-methylphenol | dark violet | +++ |
| E4-4 | 3-Amino-2-hydroxypyridine | dark blue ruby | +++ |
| E4-5 | 1,3-Bis(2,4-diaminophenoxy)propane | blue black | +++ |
| E4-6 | 2,7-Dihydroxynaphthalene | greeny brown (nutria) | ++ |

E5: N,N-dimethyl-3-[(4-amino-3-methylphenyl)amino]-N-{3-[(4-amino-3-methylphenyl)amino]propyl}-1-propanaminium p-toluene sulfonate, tetrahydrochloride

| Example | Coupler component | Obtained nuance | Color intensity |
|---|---|---|---|
| E5-1 | Resorcinol | olive brown | ++ |
| E5-2 | 3-Amino-2-methylamino-6-methoxypyridine | fir green | ++ |
| E5-3 | 5-Amino-2-methylphenol | matt violet | ++ |
| E5-4 | 3-Amino-2-hydroxypyridine | dark brown | ++ |
| E5-5 | 1,3-Bis(2,4-diaminophenoxy)propane | dark blue | ++ |
| E5-6 | 2,7-Dihydroxynaphthalene | olive | + |

E6: N-ethyl-N-methyl-3-[(4-amino-3-methylphenyl)amino]-N-{3-[(4-amino-3-methylphenyl)amino]propyl}-1-propanaminium p-toluene sulfonate, tetrahydrochloride

| Example | Coupler component | Obtained nuance | Color intensity |
|---|---|---|---|
| E6-1 | Resorcinol | olive | ++ |
| E6-2 | 3-Amino-2-methylamino-6-methoxypyridine | nickel green | ++ |
| E6-3 | 5-Amino-2-methylphenol | dark violet | ++ |
| E6-4 | 3-Amino-2-hydroxypyridine | gray brown | ++ |
| E6-5 | 1,3-Bis(2,4-diaminophenoxy)propane | dark blue | +++ |
| E6-6 | 2,7-Dihydroxynaphthalene | olive | ++ |

E7: N-methyl-N-propyl-3-[(4-amino-3-methylphenyl)amino]-N-{3-[(4-amino-3-methylphenyl)amino]propyl}-1-propanaminium p-toluene sulfonate, tetrahydrochloride

| Example | Coupler component | Obtained nuance | Color intensity |
|---|---|---|---|
| E7-1 | Resorcinol | olive brown | + |
| E7-2 | 3-Amino-2-methylamino-6-methoxypyridine | nickel green | ++ |
| E7-3 | 5-Amino-2-methylphenol | aubergine | ++ |
| E7-4 | 3-Amino-2-hydroxypyridine | gray brown | ++ |
| E7-5 | 1,3-Bis(2,4-diaminophenoxy)propane | dark blue | +++ |
| E7-6 | 2,7-Dihydroxynaphthalene | olive | ++ |

Color intensity: +++ high ++ medium + low

The invention claimed is:

1. An agent for the oxidative dyeing of keratinic fibers, the agent comprising in a cosmetic carrier a compound of the Formula (I) as an oxidation dye precursor of a developer type

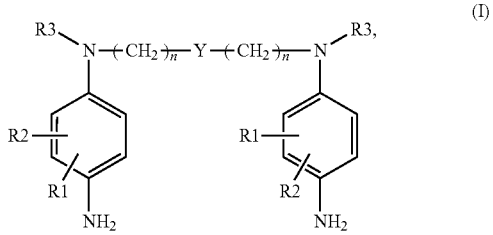

in which
R1 and R2 independently of one another stand for hydrogen, a $C_1$-$C_6$ alkyl group, a $C_2$-$C_6$ alkenyl group, a $C_1$-$C_6$ hydroxyalkyl group, a $C_2$-$C_6$ polyhydroxyalkyl group, a $C_1$-$C_6$ alkoxy group or a halogen atom,
R3 stands for hydrogen, a $C_1$-$C_6$ alkyl group, a $C_2$-$C_6$ alkenyl group, a $C_2$-$C_6$ hydroxyalkyl group, a $C_2$-$C_6$ polyhydroxyalkyl group, a $C_1$-$C_6$ alkoxy $C_2$-$C_6$ alkyl group, a cyano-$C_1$-$C_6$ alkyl group or an aryl-$C_1$-$C_6$ alkyl group,
n stands for a whole number from 2 to 6,
Y stands for a cationic moiety of the Formulas (II) to (V),

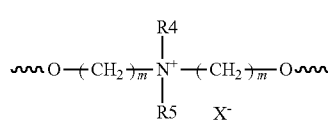

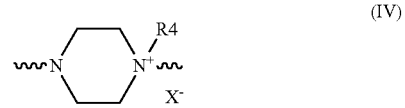

in which
R4, R5 stand independently of one another for a $C_1$-$C_6$ alkyl group, a $C_2$-$C_6$ alkenyl group, a $C_2$-$C_6$ hydroxyalkyl group, a polyhydroxy $C_2$-$C_6$ alkyl group, a $C_1$-$C_6$ alkoxy-$C_2$-$C_6$ alkyl group, a cyano $C_1$-$C_6$ alkyl group, an aryl group or an aryl $C_1$-$C_6$ alkyl group,
m stands for a whole number from 2 to 6 and
$X^-$ stands for a physiologically acceptable anion,
and/or its physiologically acceptable salt.

2. The agent according to claim 1, wherein R1 and R2 independently of one another stand for hydrogen, a $C_1$-$C_6$ alkyl group, a $C_1$-$C_6$ alkoxy group or a halogen atom.

3. The agent according to claim 1, wherein R3 stands for hydrogen or a $C_1$-$C_6$ alkyl group.

4. The agent according to claim 1, wherein Y stands for a cationic moiety of the Formulas (II) or (IV).

5. The agent according to claim 1, wherein R4 and R5 independently of one another stand for a $C_1$-$C_6$ alkyl group or a $C_2$-$C_6$ alkenyl group and/or m preferably stands for the number 2 or 3.

6. The agent according to claim 1, wherein the compound according to Formula (I) is chosen from the group of salts comprising N,N-dimethyl-3-[(4-amino-3-methylphenyl)amino]-N-{3-[(4-amino-3-methylphenyl)amino]propyl}-1-propanaminium, N-ethyl-N-methyl-3-[(4-amino-3-methylphenyl)amino]-N-{3-[(4-amino-3-methylphenyl)amino]propyl}-1-propanaminium, N-methyl-N-propyl-3-[(4-amino-3-methylphenyl)amino]-N-{3-[(4-amino-3-methylphenyl)amino]propyl}-1-propanaminium, N,N-dimethyl-3-[(4-amino-2-methylphenyl)amino]-N-{3-[(4-amino-2-methyl-phenyl)amino]propyl}-1-propanaminium, N-ethyl-N-methyl-3-[(4-amino-2-methyl-phenyl)amino]-N-{3-[(4-amino-2-methylphenyl)amino]propyl}-1-propanaminium, N-methyl-N-propyl-3-[(4-amino-2-methylphenyl)amino]-N-{3-[(4-amino-2-methylphenyl)-amino]propyl}-1-propanaminium, N1,N4-bis-{3-[(4-amino-3-methylphenyl)amino]-propyl}-N1-methylpiperazinium, N1,N4-bis-{2-[(4-amino-3-methylphenyl)amino]ethyl}-N1-methylpiperazinium, N,N-dimethyl-3-[(4-aminophenyl)amino]-N-{3-[(4-amino-phenyl)amino]propyl}-1-propanaminium, N-ethyl-N-methyl-3-[(4-aminophenyl)amino]-N-{3-[(4-aminophenyl)amino]propyl}-1-propanaminium, N-methyl-N-propyl-3-[(4-aminophenyl)amino]-N-{3-[(4-aminophenyl)amino]-propyl}-1-propanaminium, N-allyl-N-methyl-3-[(4-aminophenyl)amino]-N-{3-[(4-aminophenyl)amino]-propyl}-1-propanaminium, N1,N4-bis-{3-[(4-aminophenyl)amino]propyl}-N1-methylpiperazinium and/or N1,N4-bis-{2-[(4-aminophenyl)amino]ethyl}-N1-methylpiperazinium.

7. The agent according to claim 1, wherein the compound of the Formula (I) is present in the agent in a quantity by weight of about 0.001 to about 10.0 wt %, based on the total weight of the agent.

8. The agent according to claim 1, further comprising an oxidation dye precursor of the coupler type that is chosen from the group comprising 3-aminophenol, 5-amino-2-methylphenol, 3-amino-2-chloro-6-methylphenol, 2-hydroxy-4-aminophenoxy-ethanol, 5-amino-4-chloro-2-methylphenol, 5-(2-hydroxyethyl)-amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methyl-phenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline and their physiologically acceptable salts.

9. A compound for the oxidative dyeing of keratinic fibers, the compound having the structure of Formula (I)

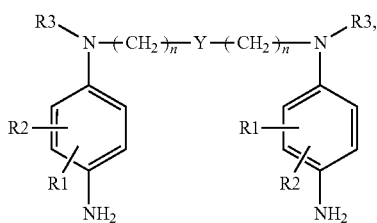

(I)

in which
R1 and R2 independently of one another stand for hydrogen, a $C_1$-$C_6$ alkyl group, a $C_2$-$C_6$ alkenyl group, a $C_1$-$C_6$ hydroxyalkyl group, a $C_2$-$C_6$ polyhydroxyalkyl group, a $C_1$-$C_6$ alkoxy group or a halogen atom,
R3 stands for hydrogen, a $C_1$-$C_6$ alkyl group, a $C_2$-$C_6$ alkenyl group, a $C_2$-$C_6$ hydroxyalkyl group, a $C_2$-$C_6$ polyhydroxyalkyl group, a $C_1$-$C_6$ alkoxy $C_2$-$C_6$ alkyl group, a cyano-$C_1$-$C_6$ alkyl group or an aryl-$C_1$-$C_6$ alkyl group,
n stands for a whole number from 2 to 6,
Y stands for a cationic moiety of the Formulas (II) to (V),

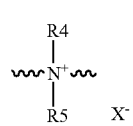

(II)

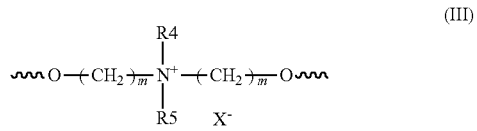

(III)

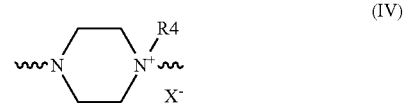

(IV)

(V)

in which
R4, R5 stand independently of one another for a $C_1$-$C_6$ alkyl group, a $C_2$-$C_6$ alkenyl group, a $C_2$-$C_6$ hydroxyalkyl group, a polyhydroxy $C_2$-$C_6$ alkyl group, a $C_1$-$C_6$ alkoxy-$C_2$-$C_6$ alkyl group, a cyano $C_1$-$C_6$ alkyl group, an aryl group or an aryl $C_1$-$C_6$ alkyl group,
m stands for a whole number from 2 to 6 and
X⁻ stands for a physiologically acceptable anion,
and/or its physiologically acceptable salt.

10. The compound according to claim 9, wherein R1 and R2 independently of one another stand for hydrogen, a $C_1$-$C_6$ alkyl group, a $C_1$-$C_6$ alkoxy group or a halogen atom.

11. The compound according to claim 9 wherein R3 stands for hydrogen or a $C_1$-$C_6$ alkyl group.

12. The compound according to claim 1, wherein Y stands for a cationic moiety of the Formulas (II) or (IV).

13. The compound according to claim 1, wherein R4 and R5 independently of one another stand for a $C_1$-$C_6$ alkyl group or a $C_2$-$C_6$ alkenyl group and/or m preferably stands for the number 2 or 3.

14. The compound according to claim 1, wherein the compound according to Formula (I) is chosen from the group of salts comprising N,N-dimethyl-3-[(4-amino-3-methylphenyl)amino]-N-{3-[(4-amino-3-methylphenyl)amino]propyl}-1-propanaminium, N-ethyl-N-methyl-3-[(4-amino-3-methylphenyl)amino]-N-{3-[(4-amino-3-methylphenyl)amino]propyl}-1-propanaminium, N-methyl-N-propyl-3-[(4-amino-3-methylphenyl)amino]-N-{3-[(4-amino-3-methylphenyl)amino]propyl}-1-propanaminium, N,N-dimethyl-3-[(4-amino-2-methylphenyl)amino]-N-{3-[(4-amino-2-methyl-phenyl)amino]propyl}-1-propanaminium, N-ethyl-N-methyl-3-[(4-amino-2-methyl-phenyl)amino]-N-{3-[(4-amino-2-methylphenyl)amino]propyl}-1-propanaminium, N-methyl-N-propyl-3-[(4-amino-2-methylphenyl)amino]-N-{3-[(4-amino-2-methylphenyl)-amino]propyl}-1-propanaminium, N1,N4-bis-{3-[(4-amino-3-methylphenyl)amino]-propyl}-N1-methylpiperazinium, N1,N4-bis-{2-[(4-amino-3-methylphenyl)amino]ethyl}-N1-methylpiperazinium, N,N-dimethyl-3-[(4-aminophenyl)amino]-N-{3-[(4-amino-phenyl)amino]propyl}-1-propanaminium, N-ethyl-N-methyl-3-[(4-aminophenyl)amino]-N-{3-[(4-aminophenyl)amino]propyl}-1-propanaminium, N-methyl-N-propyl-3-[(4-aminophenyl)amino]-N-{3-[(4-aminophenyl)amino]-propyl}-1- propanaminium, N-allyl-N-methyl-3-[(4-aminophenyl)amino]-N-{3-[(4-aminophenyl)amino]-propyl}-1-propanaminium, N1,N4-bis-{3-[(4-aminophenyl)amino]propyl}-N1-methylpiperazinium and/or N1,N4-bis-{2-[(4-aminophenyl)amino]ethyl}-N1-methylpiperazinium.

* * * * *